US011939572B2

(12) United States Patent
Kisielow et al.

(10) Patent No.: US 11,939,572 B2
(45) Date of Patent: Mar. 26, 2024

(54) CHIMERIC ANTIGEN RECEPTORS AND METHODS OF USE

(71) Applicant: ETH Zürich, Zurich (CH)

(72) Inventors: Jan Kisielow, Schlieren (CH); Franz-Josef Obermair, Oberengstringen (CH); Manfred Kopf, Zurich (CH)

(73) Assignee: ETH Zürich, Zurich (CH)

( * ) Notice: Subject to any disclaimer, the term of this patent is extended or adjusted under 35 U.S.C. 154(b) by 672 days.

(21) Appl. No.: 17/098,226

(22) Filed: Nov. 13, 2020

(65) Prior Publication Data

US 2021/0123042 A1 Apr. 29, 2021

Related U.S. Application Data

(62) Division of application No. 15/537,418, filed as application No. PCT/EP2015/080576 on Dec. 18, 2015, now Pat. No. 10,865,408.

(30) Foreign Application Priority Data

Dec. 19, 2014 (EP) .................................... 14199148

(51) Int. Cl.

| | |
|---|---|
| ***C07K 14/74*** | (2006.01) |
| ***A61K 35/17*** | (2015.01) |
| ***C07K 14/725*** | (2006.01) |
| ***C12N 5/0783*** | (2010.01) |
| ***C12N 15/10*** | (2006.01) |
| ***G01N 33/50*** | (2006.01) |

(52) U.S. Cl.

CPC .......... *C12N 15/1055* (2013.01); *A61K 35/17* (2013.01); *C07K 14/7051* (2013.01); *C07K 14/70539* (2013.01); *C12N 5/0636* (2013.01); *G01N 33/505* (2013.01); *C07K 2319/03* (2013.01); *C07K 2319/40* (2013.01); *C07K 2319/60* (2013.01); *C07K 2319/61* (2013.01)

(58) Field of Classification Search

None

See application file for complete search history.

(56) References Cited

U.S. PATENT DOCUMENTS

| | | | |
|---|---|---|---|
| 10,865,408 | B2 | 12/2020 | Kisielow et al. |
| 2004/0253632 | A1 | 12/2004 | Rhode et al. |
| 2008/0286312 | A1 | 11/2008 | Gross et al. |
| 2019/0345485 | A1 | 11/2019 | Kisielow et al. |

FOREIGN PATENT DOCUMENTS

| | | | |
|---|---|---|---|
| CN | 103249430 | A | 8/2013 |
| WO | 2008/041231 | A2 | 4/2008 |
| WO | 2014018863 | A1 | 1/2014 |
| WO | 2014127261 | A1 | 8/2014 |

OTHER PUBLICATIONS

Anel et al., Eur. J. Immunol. 1996.26: 2310-2319. (Year: 1996).*
U.S. Appl. No. 15/537,418, filed Jun. 18, 2017, Jan Kisielow.
U.S. Appl. No. 15/537,418, filed Aug. 26, 2020, Z. Skelding.
U.S. Appl. No. 15/537,418, filed Dec. 13, 2019, Z. Skelding.
U.S. Appl. No. 15/537,418, filed Sep. 12, 2019, Z. Skelding.
Brogdon, J. et al., "A site for CD4 binding in the beta 1 domain of the MHC class II protein HLA-DR1," J Immunol., vol. 161:5472-5480. (1998).
Geiger, T. et al., "Integrated Src Kinase and Costimulatory Activity Enhances Signal Transduction Through Single-Chain Chimeric Receptors in T Lymphocytes," Blood, vol. 98(8) 2364-2371 (2001).
Jyothi M.D. et al.: "Targeting autoantigen-specific T cells and suppression of autoimmune encephalyomelitis with receptor-modified T lymphocyes", Nat. Biotechnol., vol. 20, No. 12, Dec. 2002, pp. 1215-1220.
Kuhns, M. et al., "TCR Signaling Emerges from the Sum of Many Parts," Frontiers in Immunology, vol. 3 (Article 159): p. 1-13. (2012).
Li, Y. et al., "Structural and biophysical insights into the role of CD4 and CD8 in T cell activation," Front Immunol. J., vol. 4:206 (2013).
Liu, J. et al., Major Histocompatibility Complex: Interaction with Peptides, ELS, John Wiley & Sons, Ltd: Chichester. (2011) pp. 1-12.Chichester. pp. 1-12 (2011).
Macian, F., "NFAT proteins: key regulators of T-cell development and function," Nat Rev Immunol., vol. 5(6):472-84 (2005).
Mekala, D. et al., "IL-10-dependent Infectious Tolerance After the Treatment of Experimental Allergic Encephalomyelitis With Redirected CD4+CD25+ T Lymphocytes," PNAS, vol. 102(33):11817-11822 (2005).

(Continued)

*Primary Examiner* — Zachary S Skelding
(74) *Attorney, Agent, or Firm* — Goodwin Procter LLP

(57) ABSTRACT

The invention relates to a chimeric antigen-receptor polypeptide heterodimer comprising two polypeptides, wherein the first contains an extracellular part of the major histocompatibility complex I alpha chain and the second contains a 32-microglobulin domain, or the first contains an extracellular part of the major histocompatibility complex II alpha chain and the second contains a major histocompatibility complex II beta chain. One of the polypeptides further contains a transmembrane domain, a hinge region and an intracellular domain of the T cell receptor alpha chain and the other one contains a transmembrane domain, a hinge region and an intracellular domain of the T cell receptor beta chain, and additionally an antigen-peptide covalently linked to said extracellular MHC domain. The invention further relates to a method for the identification of a TCR recognizable peptide sequence making use of the heterodimer of the invention.

10 Claims, 10 Drawing Sheets

Figure 1:
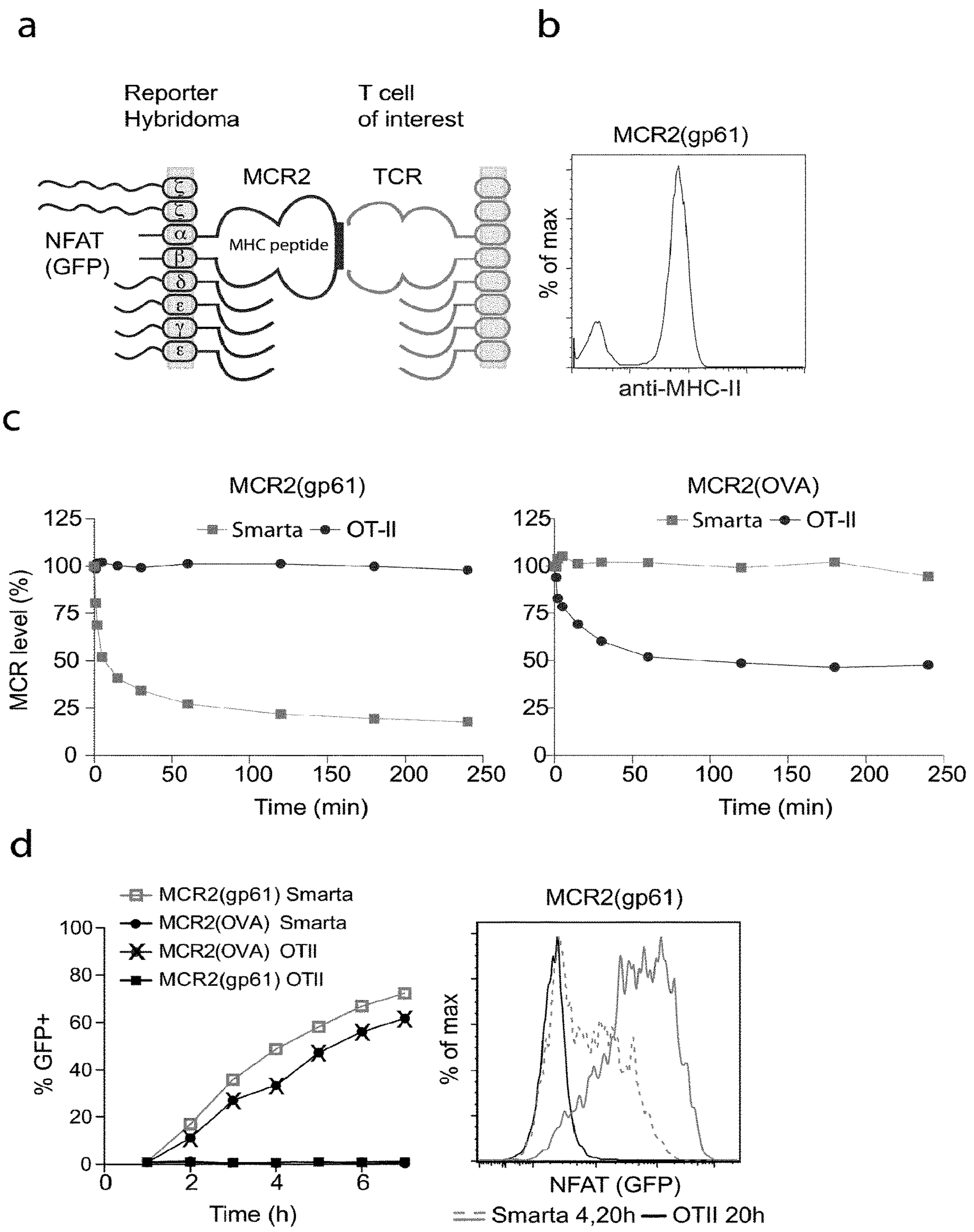
Figure 1:
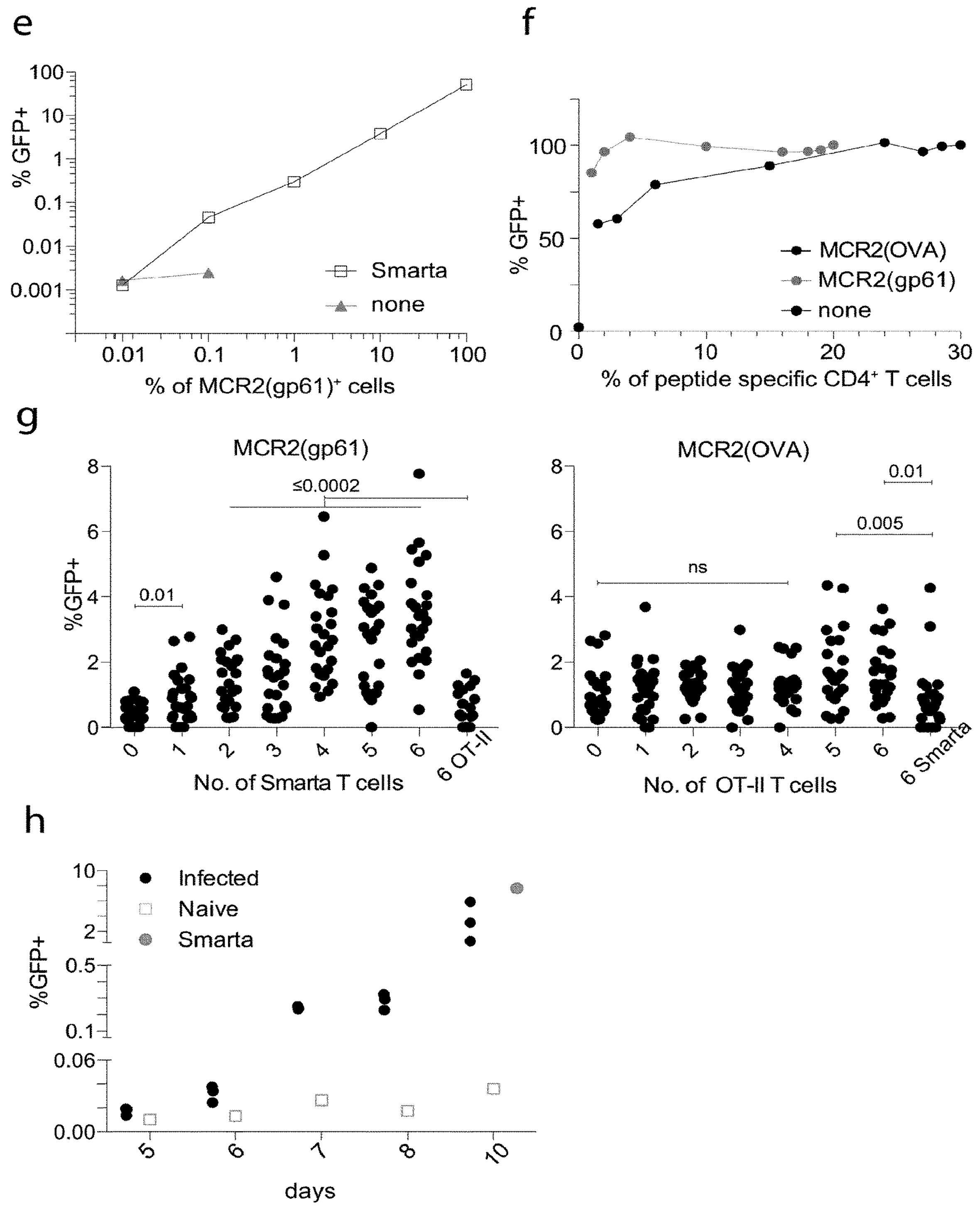

Specification includes a Sequence Listing.

(56) References Cited

OTHER PUBLICATIONS

Moisini et al., "Redirecting Therapeutic T Cells Against Myelin-Specific T Lymphocytes Using a Humanized Myelin Basic protein-HLA-DR2-zeta Chimeric Receptor," J Immunol., vol. 180:3601-3611 (2008).
Painter, C. et al., "Conformational variation in structures of classical and non-classical MHCII proteins and functional implications," Immunological Reviews, vol. 250: 144-157 (2012).
Richman S.A. et al., "Display, engineering, and applications of antigen-specific T cell receptors", Biomol. Engineer., vol. 24 (4):361-373 (2007).
Sadelain M. et al., "The basic principles of chimeric antigen receptor design", Cancer Discovery, vol. 3(4): 388-398 (2013).
Scott, G. et al., "Immunotargeting of Insulin Reactive CD8 T Cells to Prevent Diabetes," J Autoimm., vol. 35:390-397 (2010).
Wucherpfennig, K. et al., "Structural biology of the T-cell receptor: insights into receptor assembly, ligand recognition, and initiation of signaling," Cold Spring Harb Perspect Biol., vol. 2(4):a005140 (2010).
Xu, C. et al., "A membrane-proximal tetracysteine motif contributes to assembly of CD3deltaepsilon and CD3gammaepsilon dimers with the T cell receptor," JBC, vol. 281 (48): 36977-36984 (2006).
Yin, Y. et al., "Crystal structure of a complete ternary complex of T-cell receptor, peptide-MHC, and CD4," Proc Natl Acad Sci., vol. 109(14):5405-5410 (2012).
Zhang T. et al.: "SING: a novel strategy for identifying tumor-specific, cytotoxic T lymphocyte-recognized tumor antigens", The FASEB Journal, Jan. 20, 2004, XP055186140, Retrieved from the Internet:URL:http://www.fasebj.org/content/early/20/04/03/05/fj.03-0881fje.full.pdf.
Zhao, T., "T Cell receptor diversity and its biological significance," Shanghai Journal of Immunology, Dec. 31, 1997; 17(1):4-8.

* cited by examiner

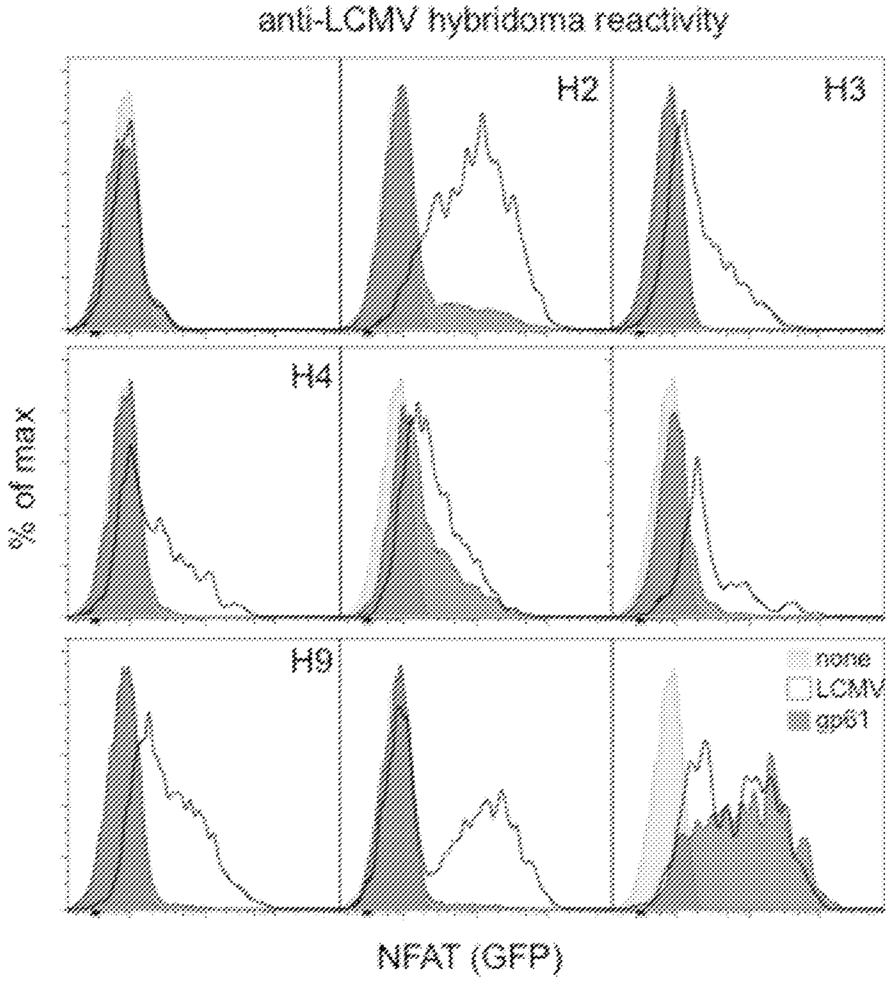
FIG. 3A
anti-LCMV hybridoma reactivity
| | day5 | day8 | Total |
|---|---|---|---|
| gp61 | 7 | 21 | 28 |
| non-gp61 | 6 | 8 | 14 |
| none | 8 | 17 | 25 |
FIG. 3B
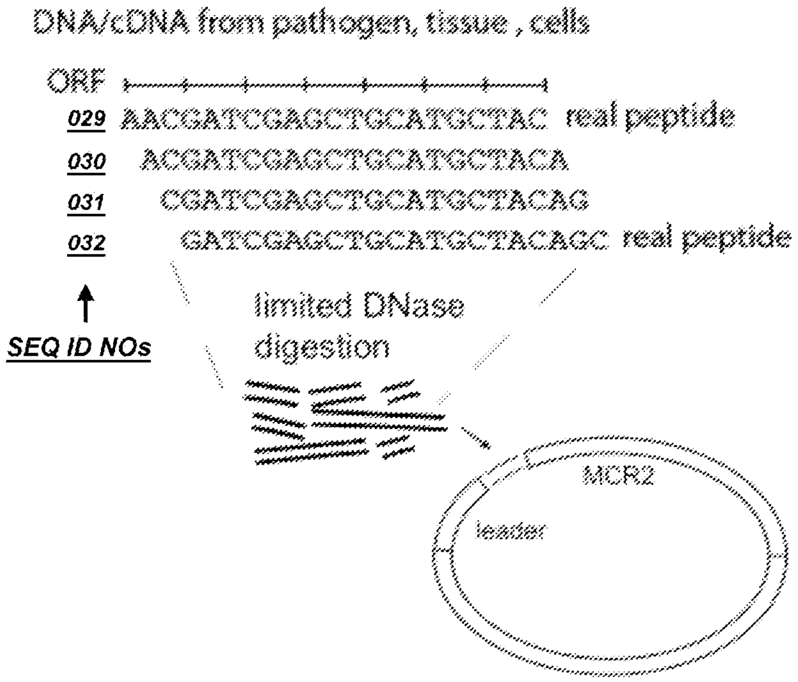
FIG. 3C

| Hybridoma | Clones Responding/Screened |
|---|---|
| H2 | 10/10 |
| H3 | 10/10 |
| H14 | 8/10 |
| H30 | 10/10 |

033 H2,H14,H30: GAGGGGTGGCCATACATAGCTTGTAGAACATCAGTTGTAGGGAGA

034 NP311 E G W P Y I A C R T S V V G R

035 H3: GACCTGATCTTCAGAGGTCCAAATGTGGTG

036 NP547 D L I F R G P N V V

↑ SEQ ID NOs

Reporter clones responding to H9

SEQ ID NOs

| SEQ ID NO | | | | | | | | | | | | | | | |
|---|---|---|---|---|---|---|---|---|---|---|---|---|---|---|---|
| 006 | DNA | GGTNNNNNNTWCNNNNNNBCCNNNSCCNNNNNNKCCNNNGGA | | | | | | | | | | | | | |
| 037 | | G | x | x | Y/F | x | x | PAS | x | A/P | x | x | A/S | x | G |
| | Library (example sequences) | | | | | | | | | | | | | | |
| 038 | 7 | G | G | G | Y | S | A | S | C | P | V | I | A | P | G |
| 039 | 8 | G | R | R | Y | K | * | A | T | A | S | I | A | F | G |
| 040 | 9 | G | N | I | F | F | I | S | T | A | S | I | A | N | G |
| 041 | 10 | G | T | M | F | L | N | A | S | P | G | N | S | E | G |
| 042 | 12 | G | T | D | Y | * | L | S | A | A | R | S | S | D | G |
| | H9-specific peptides | | | | | | | | | | | | | | |
| 043 | A1 | G | G | R | Y | H | R | P | L | P | C | A | S | P | G |
| 044 | A2 | G | R | G | Y | I | S | A | Y | P | H | F | S | I | G |
| 045 | D3 | G | G | I | F | N | R | A | L | P | A | P | S | K | G |

CHIMERIC ANTIGEN RECEPTORS AND METHODS OF USE

This Application is a Division of U.S. patent application Ser. No. 15/537,418 filed on Jun. 18, 2017, which is a 35 U.S.C. 371 national stage filing of International Application No. PCT/EP2015/080576, which claims priority to European Patent Application 14199148.9 filed on Dec. 19, 2014. The entire contents of these applications are incorporated herein by reference in their entirety.

SEQUENCE LISTING

The instant application contains a Sequence Listing which has been submitted via EFS-Web and is hereby incorporated by reference in its entirety. Said ASCII copy, created on Nov. 13, 2020, is named Sequence_Listing_COJ_002USDV.txt and is 16799 bytes in size.

Most T-cells express αβT-cell receptors (TCRs) and recognize antigens in the form of peptides (epitopes) presented by the major histocompatibility complex (MHC) on other cells. The TCRs of cytotoxic T-lymphocytes recognise epitopes displayed by MHC class I molecules on the surface of almost every cell in the body. The TCRs of helper T cells recognise epitopes displayed by MHC class II molecules on the surface of antigen-presenting immune cells, including macrophages, dendritic cells and B-cells. Efficient recognition of the epitope by T cells involves additional T cell surface glycoproteins: CD8 on cytotoxic T-lymphocytes ($CD8^+$ T cells), and CD4 on helper T cells ($CD4^+$ T cells), which bind MHC class I and II molecules, respectively. The binding of a TCR to an epitope can result in signals being sent to the T lymphocyte's nucleus to induce a T cell response.

Unambiguous and efficient identification of antigenic specificities of T cells holds great promise for the development of efficient immune therapies and diagnostic tools. In particular:

- it may help assessing the safety of adoptive T cell therapies,
- it may enable new approaches in the treatment of autoimmune diseases, cancer, and in the development of new vaccines.

However, TCRs bind MHC-peptide complexes with low affinity, which makes phage- and yeast-display methods inefficient. Alternative methods, like screening of positional scanning combinatorial peptide libraries, take advantage of the cross-reactivity of the TCR and use peptide pools to define motifs that lead to T-cell activation. Apart from similar affinity constrains, these cumbersome methods suffer from a high rate of false-positive results. Because random peptide sequences are interrogated, the identified peptide motifs are ambiguous or have no clear homology to native proteins.

The problem underlying the present invention is to provide the means for direct and sensitive, unbiased identification of antigenic peptide specificities of $CD4^+$ and $CD8^+$ T cells for use in vitro and in vivo. This problem is solved by the subject-matter of the independent claims.

TERMS AND DEFINITIONS

Amino acid sequences are given from amino to carboxyl terminus. Capital letters for sequence positions refer to L-amino acids in the one-letter code (Stryer, Biochemistry, $3^{rd}$ ed. p. 21). Lower case letters for amino acid sequence positions refer to the corresponding D- or (2R)-amino acids.

In the context of the present invention, the terms identity or sequence identity are used in their meaning known in the art of genetics and bioinformatics; they refer to a single quantitative parameter representing the result of a sequence comparison position by position. Methods of sequence comparison are known in the art; the BLAST algorithm available publicly is an example.

One such example for comparison of amino acid sequences is the BLASTP algorithm that uses default settings such as: Expect threshold: 10; Word size: 3; Max matches in a query range: 0; Matrix: BLOSUM62; Gap Costs: Existence 11, Extension 1; Compositional adjustments: Conditional compositional score matrix adjustment. In the absence of further details, these settings are used for determination of amino acid sequence identity values given below.

One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. In the absence of further details, these settings are used for determination of nucleic acid sequence identity values given below.

In the context of the present specification, the term major histocompatibility complex (MHC) is used in its meaning known in the art of cell biology and biochemistry; it refers to a cell surface molecule that displays a peptide, a fraction of a protein, in a way suitable for the recognition by a T cell receptor. Peptides recognised by the immune system are referred to as epitopes or antigenic peptides or oligopeptides in the context of the present specification.

There are two major classes of MHC molecules: class I and class II.

MHC class I occurs as α chain composed of three domains—α1, α2, α3. The α3 domain interacts with the non-MHC molecule β2-microglobulin. The peptide being displayed or presented is held by the peptide-binding groove, in the central region of the α1/α2 heterodimer. The α3 subunit contains a transmembrane domain, anchoring the MHC class I molecule to the cell membrane.

MHC class II is formed of two chains, α and β, each having two domains—α1 and α2 and β1 and β2, respectively. The peptide-binding groove (the structural element formed by the MHC class II molecule that presents or displays the peptide epitope) is formed by the heterodimer of α1 and β1. The α2 and β2 subunits contain transmembrane domains anchoring the MHC class II molecule to the cell membrane.

MHC class I and class II molecules comprise in their immature form a signal peptide like the majority of newly synthesized proteins that are destined towards the secretory pathway. The MHC signal peptide sequence is located upstream (5') of the MHC α1 domain on the MHC mRNA molecule. After cleavage of the signal peptide the MHC molecule is referred to as the mature MHC molecule.

In the context of the present specification, the term β2-microglobulin domain is used in its meaning known in the art of cell biology and biochemistry; it refers to a non-MHC molecule that is part of the MHC class I heterodimer molecule. In other words, it constitutes the β chain of the MHC class I heterodimer.

In the context of the present specification, the term T cell receptor (TCR) is used in its meaning known in the art of cell biology and biochemistry; it refers to a molecule found on the surface of T cells that is able to recognize antigens bound to major histocompatibility complex molecules. TCRs are disulfide-linked membrane-anchored heterodimers consisting of highly variable α and β chains. Each chain is composed of two extracellular domains: Variable (V) region and a Constant (C) region. The Variable region binds to the peptide-MHC complex; the Constant region is proximal to the cell membrane, followed by a hinge region, transmembrane region and a short cytoplasmic tail.

In the context of the present specification, the term T cell receptor complex is used in its meaning known in the art of cell biology and immunology; it refers to an octameric complex of the heterodimeric TCRα/β, with two heterodimeric signaling modules CD3ε/δ and CD3γ/ε and the homodimer CD247ζ/ζ (also known as TCR ζ-chain or zeta-chain). Ionizable residues in the transmembrane domain of each subunit form a polar network of interactions that hold the complex together. Since the cytoplasmic tail of the TCRα/β is extremely short, making it unlikely to participate in signaling, these signaling molecules are vital in propagating the signal from the triggered TCR into the cell. The most common mechanism for activation and regulation of molecules beneath the plasma membrane is via phosphorylation/dephosphorylation by protein kinases. The intracellular parts of CD3 and CD247ζ contain immunoreceptor tyrosine-based activation motifs (ITAMs) that are targeted by the Src family of tyrosine-kinases.

In the context of the present specification, the term functionally linked refers to the linkage of the activity status of two different functions. For example a receptor polypeptide (function 1) may be functionally linked to a reporter gene and its promoter (function 2); then, if the receptor changes its activity status (e.g. activated), the promoter of the reporter gene will also change its activity status (e.g. activated) and the reporter gene is transcribed. One such non-limiting example is the nuclear factor of activated T cells (NFAT) signaling pathway known in the art. Activation of native TCRs (function 1) in T cells results in the activation of protein kinases and phosphatases that initiate nuclear import of the transcription factor NFAT leading to the expression of NFAT target genes (function 2). In other words the TCR is functionally linked to the expression of NFAT target genes.

In the context of the present specification, the term activation of the reporter gene refers to a change in the activity status of the reporter gene. One example of such a change in activity status is the activation of the promoter of a reporter gene. This results in the increased transcription/translation of the reporter gene. Another example is the cleavage of an inhibitor of the reporter protein which results in an increased amount of active reporter protein.

In the context of the present specification, the term transgenic is used in its meaning known in the art of cell biology; it refers to the introduction of a exogenous nucleic acid sequence into a living organism so that this organism displays a new property it does not possess endogenously.

In the context of the present specification, the term antigen receptor is used in its meaning known in the art of cell biology and immunology; it refers to surface receptors able to bind antigens or epitopes. Examples for antigen receptors are B-cell and T-cell receptors.

In the context of the present specification, the term chimeric antigen receptor refers to artificial engineered receptors comprising parts of antigen receptors. A non-limiting example is a hybrid receptor that comprise domains from T-cell or B-cell receptors fused to MHC domains and/or antigenic peptide sequences.

In the context of the present specification, the term oligopeptide or oligopeptide sequence exclusively refers to T-cell reactive oligopeptides that, when presented in the context of an MHC molecule on a cell, may elicit a T-cell response if recognized by a cognate T cell receptor. Where mention is made of an oligopeptide sequence being comprised in a (longer) polypeptide of the invention, the skilled person will understand that this refers to an oligopeptide sequence that can be recognized by a TCR when presented on an MHC molecule. The oligopeptide sequence comprises, in addition to the MHC-presented T cell reactive epitope, a linker of several amino acids, allowing the T cell reactive epitope to fit into the MHC molecule. Examples for linker length and sequence are given below.

According to a first aspect of the invention, a method for the identification of a TCR recognizable peptide sequence is provided, comprising the steps of:

i. Providing a plurality of mammalian cells, wherein
   - each of the plurality of mammalian cells expresses a member of a library,
   - each member of the library encodes a transgenic antigen receptor molecule,
   - the transgenic antigen receptor molecule comprises
     - an extracellular domain of MHC1 or MHC2,
     - an oligopeptide comprised within the polypeptide sequence of the extracellular domain sequence (the term within is meant to signify that the oligopeptide can be comprised anywhere between the N and C boundary of the extracellular domain sequence, or at any of its respective ends), wherein the oligopeptide is different for each member of the library, and wherein the oligopeptide is presented in a way suitable for the recognition by a T cell receptor,
     - a transmembrane domain of a T-cell receptor (TCR), and
     - an intracellular domain of a TCR,
   - the transgenic antigen receptor molecule is functionally linked to a reporter protein, whereby binding of a cognate T cell receptor to the transgenic antigen receptor results in the activation of the reporter gene.

ii. Contacting the plurality of mammalian cells with a preparation of T-lymphocytes able to bind to the oligopeptide sequence comprised in the transgenic antigen receptor through a T cell receptor expressed on the surface of the T lymphocytes.

iii. Separating cells with a detectable reporter protein from said plurality of mammalian cells according to the level of detectable reporter protein, thereby yielding activated cells.

iv. Isolating DNA encoding the expressed library member from the activated cells.

v. Sequencing of the oligopeptide sequence comprised in the transgenic antigen-receptor expressed in the activated cells. The determined sequence of the oligopeptide is the TCR recognizable peptide sequence.

In other words, the method of the invention allows assessing the antigenic potential of oligopeptides, or—to be more precise—the potential of a particular oligopeptide sequence to be a MHC-presented epitope triggering a cognate TCR response. To accomplish this assessment, a library of transgenic antigen receptors comprising potentially antigenic oligopeptides is required. A member of the library is expressed in each mammalian cell of the plurality of cells, wherein the oligopeptide sequence can be different for each member of the library. The oligopeptide is presented by the transgenic antigen receptor in a way that is suitable for the recognition by a T cell receptor. Binding of the antigenic oligopeptide by the provided T lymphocytes via their T cell receptor activates the reporter protein that is functionally linked to the transgenic antigen receptor. The mammalian cell is then separated according to the level of detectable reporter. DNA is isolated from the separated mammalian cell and the comprised oligopeptide DNA is sequenced. Every oligopeptide retrieved by this method is recognized by a T cell receptor.

The transgenic antigen receptor comprises an oligopeptide that is presented in a way suitable for the recognition by a T cell receptor, an extracellular domain of MHC1 or MHC2, a transmembrane domain of a T cell receptor and an intracellular domain of a T cell receptor. The oligopeptide and the different domains are covalently linked to form a single polypeptide chain (extracellular-transmembrane-intracelluar). In certain embodiments, the transgenic receptor additionally comprises a hinge region of a T cell receptor that is situated between the extracellular domain and the transmembrane domain.

In the context of the present specification, the terms expresses or expression are used in their meaning in the art of cell biology and molecular biology; they refer to the transcription and translation of a DNA sequence and the derived mRNA.

In certain embodiments the separation of cells with a detectable reporter protein from the plurality of mammalian cells according to the level of detectable reporter protein as described in step iii. is performed at least 1, 2, 3, 4, 5, 6, 7, 8, 9 or 10 times. This embodiment is particularly advantageous if libraries of high complexity are used.

According to an alternative aspect of the invention, a method for the identification of a TCR recognizable peptide sequence is provided. The method comprises:

- i. Providing a mammalian cell, wherein
  - the mammalian cell expresses a transgenic antigen receptor molecule;
  - the transgenic antigen receptor molecule comprises
    - an extracellular domain of MHC1 or MHC2 comprising an oligopeptide presented in a way suitable for the recognition by a T cell receptor,
    - a transmembrane domain of a T-cell receptor (TCR), and
    - an intracellular domain of a TCR,
  - the transgenic antigen receptor molecule is functionally linked to a reporter protein, whereby binding of a T cell receptor to the transgenic antigen receptor results in the activation of said reporter gene.
- ii. Contacting the mammalian cell with a preparation of T-lymphocytes able to bind to the oligopeptide comprised in the transgenic antigen receptor through a T cell receptor expressed on the surface of the T lymphocyte. Binding of the T cell receptor to the transgenic antigen receptor activates the reporter gene, yielding an activated mammalian cell.
- iii. Isolating DNA encoding the expressed library member from the activated mammalian cell.
- iv. Sequencing of the oligopeptide sequence comprised in the transgenic antigen-receptor.

In certain embodiments the transgenic antigen receptor additionally comprises a hinge region.

In certain embodiments according to the first and second aspect of the invention the transgenic antigen receptor is a transgenic antigen receptor already known in the art. Examples of suitable transgenic antigen receptors known in the art are disclosed in Jyothi et al., Nat Biotechnol 20, 1215-1220 (2002); Geiger et al., Blood 98(8) 2364-2371 (2001); US2008286312A1; Mekala et al., PNAS 102(33), 11817-11822, (2005); Moisini et al., J Immunol (2008), 180:3601-3611; Scott et al., J Autimm 35, 390-397 (2010).

In certain embodiments of any of the above aspects of the invention, the transgenic antigen receptor is a chimeric antigen-receptor polypeptide heterodimer comprising a first polypeptide and a second polypeptide, and

- a. the first polypeptide comprises an extracellular part of the major histocompatibility complex I (MHC class I) alpha chain and the second polypeptide comprises a β2-microglobulin domain, or
- b. the first polypeptide comprises an extracellular part of the major histocompatibility complex II (MHC class II) alpha chain and the second polypeptide comprises an extracellular part of the major histocompatibility complex II (MHC class II) beta chain.

At least one of the first and the second polypeptide chain additionally comprises an oligopeptide, covalently linked to the extracellular MHC domain, wherein the oligopeptide can be recognized by a T cell receptor.

In certain embodiments, the oligopeptide sequence further comprises a linker sequence 4 to 16 amino acids, particularly 6, 8, 10, 12 or 14 amino acids in length. In certain embodiments, the linker is predominantly composed of glycine and one of serine, threonine and alanine. In certain embodiments, the linker comprises glycine and serine only.

One of the first polypeptide and the second polypeptide further comprises a hinge region, a transmembrane domain and an intracellular domain or intracellular tail of the T cell receptor alpha chain and the other one of the first polypeptide and the second polypeptide comprises a hinge region, a transmembrane domain and an intracellular domain of the T cell receptor beta chain.

In certain embodiments the oligopeptide sequence and a glycine-serine linker are inserted between the last amino acid of the MHC signal/leader peptide and the first amino acid of the MHC α1 domain or β1 domain.

In certain embodiments the oligopeptide sequence and a linker sequence is inserted after amino acid 1, 2, 3, 4 or 5 of the MHC α1 domain sequence or β1 domain sequence.

Attaching the peptide to the beta chain (β1 domain) will insert the peptide into the MHC in the most commonly found direction. Attaching it to the alpha chain will insert the peptide in a reverse orientation.

In certain embodiments the extracellular part of the MHC molecule is selected from the human major histocompatibility complex gene family HLA available to the person skilled in the art in specialist databases such as IMGT/HLA (http://www.ebi.ac.uk/ipd/imgt/hla/). Alternatively, the HLA sequence is derived from the RNA extracted from patient blood or tissue samples.

In certain embodiments the oligopeptide is 8, 9, 10, 11, 12, 13, 14, 15, 16, 17, 18, 19, 20, 25, 30 or 40 amino acids (AA) in length. The majority of MHC class I peptides are 8-10 amino acids long whereas MHC class II can present much longer peptides, as the binding cleft is open, nevertheless the actual epitope ranges from 10 to 12 AA. In the herein disclosed method the peptides might be even longer than 20 (see FIG. 3, the LCMV peptide found by the method of invention comprises 24 AA). In certain embodiments, larger oligopeptides are employed, as this allows screening of more binding registers on one peptide.

In certain embodiments the hinge region, the transmembrane and intracellular part of the transgenic antigen-receptor in the first and/or second polypeptide is not derived from the same TCR chain. In other words the hinge region or the transmembrane domain of the TCR α-chain could be connected to the transmembrane or intracellular domain of the TCR β-chain and vice versa.

In certain embodiments the chimeric antigen-receptor polypeptide heterodimer according to the second aspect of the invention, comprises a first polypeptide with an amino acid sequence having at least ≥80%, 85%, 90%, 92%, 94%, 95%, 96%, 97%, 98% or 99% identity to SEQ ID NO 007 and a second polypeptide with an amino acid sequence having at least ≥80%, 85%, 90%, 92%, 94%, 95%, 96%, 97%, 98% or 99% identity to SEQ ID NO 008.

According to a third aspect of the invention a chimeric antigen-receptor polypeptide heterodimer is provided comprising a first polypeptide and a second polypeptide. The first polypeptide is linked to the second polypeptide by one or several disulfide bonds, and a. the first polypeptide comprises an extracellular part of the major histocompatibility complex I (MHC class I) alpha chain and the second polypeptide comprises a major histocompatibility complex I (MHC class I) associated β2-microglobulin domain, or
b. the first polypeptide comprises an extracellular part of the major histocompatibility complex II (MHC class II) alpha chain and the second polypeptide comprises a major histocompatibility complex II (MHC class II) beta chain.

One of the first polypeptide and the second polypeptide further comprises a hinge region, transmembrane domain (and the intracellular domain or tail) of the T cell receptor (TCR) alpha chain and the other one of the first polypeptide and the second polypeptide comprises a hinge region, transmembrane domain (and the intracellular domain or tail) of the T cell receptor beta chain.

In other words the chimeric antigen-receptor polypeptide heterodimer is able to present an oligopeptide (epitope) in an MHC-context, in order for the oligopeptide (epitope) to be recognized and bound by its cognate TCR. The binding of its cognate TCR results in the activation of the intracellular domains of the CD3 and CD247 molecules associated with the chimeric antigen-receptor polypeptide heterodimer, which leads to the activation of NFAT.

In certain embodiments, the extracellular parts of the MHC molecule comprise i. MHC class I alpha1 and alpha2 and alpha3 domains on the first polypeptide (in addition to β-2 microglobulin as the second polypeptide), or
ii. MHC class II alpha1 and alpha2 domains on the first polypeptide, and MHC class II beta1 and beta2 domains on the second polypeptide.

In certain embodiments, the first polypeptide comprises substantially the entire extracellular part of the major histocompatibility complex I (MHC class I) alpha chain. In certain embodiments, the first polypeptide is the extracellular part of the major histocompatibility complex I (MHC class I) alpha chain.

In certain embodiments, the second polypeptide comprises substantially the entire extracellular part of the major histocompatibility complex I (MHC class I) associated β2-microglobulin domain. In certain embodiments, the second polypeptide is the major histocompatibility complex I (MHC class I) associated β2-microglobulin domain.

In certain other embodiments, the first polypeptide comprises substantially the entire extracellular part of the major histocompatibility complex II (MHC class II) alpha chain. In certain embodiments, the first polypeptide is the extracellular part of the major histocompatibility complex II (MHC class II) alpha chain. In certain embodiments, the second polypeptide comprises substantially the entire major histocompatibility complex II (MHC class II) beta chain. In certain embodiments, the second polypeptide is the major histocompatibility complex II (MHC class II) beta chain.

In certain embodiments at least one of the first and the second polypeptide chain additionally comprises an antigen-peptide covalently linked to the extracellular MHC domain, wherein said oligopeptide can be recognized by a T cell receptor.

In certain embodiments the antigen-peptide sequence and a glycine-serine linker are inserted between the last amino acid of the MHC signal/leader peptide and the first amino acid of the MHC α1 domain or β1 domain.

In certain embodiments the antigen-peptide sequence and a linker sequence is inserted after amino acid 1, 2, 3, 4 or 5 of the MHC α1 domain sequence or β1 domain sequence.

In certain embodiments the extracellular part of the MHC molecule is selected from the human major histocompatibility complex gene family HLA available in specialist databases such as IMGT/HLA (http://www.ebi.ac.uk/ipd/imgt/hla/). Alternatively, the HLA sequence is derived from the RNA extracted from patient blood or tissue samples.

In certain embodiments the oligopeptide is 8, 9, 10, 11, 12, 13, 14, 15, 16, 17, 18, 19, 20, 25, 30 or 40 amino acids in length. The majority of MHC class I peptides are 8-10 amino acids long whereas MHC class II can present much longer peptides, as the binding cleft is open, nevertheless the actual epitope is inside 10-12 AA. In the herein disclosed method the peptides might be even longer than 20 (see FIG. 3, the LCMV peptide found by the method of invention comprises 24 AA). It could be advantageous to have larger oligopeptides as this allows screening of more binding registers on one peptide.

In certain embodiments the hinge region, the transmembrane and intracellular part of the chimeric antigen-receptor polypeptide in the first and/or second polypeptide is not derived from the same TCR chain. In other words the hinge region or the transmembrane domain of the TCR α-chain could be connected to the transmembrane or intracellular domain of the TCR β-chain and vice versa.

According to a fourth aspect of the invention a nucleic acid molecule encoding the chimeric antigen-receptor polypeptide heterodimer according to the third aspect of the invention is provided, particularly a nucleic acid molecule having a promoter sequence operable in a mammalian host cell.

According to a fifth aspect of the invention a cell, particularly a mammalian cell, comprising or expressing the nucleic acid molecule according to the fourth aspect of the invention is provided.

According to a sixth aspect of the invention a cell, particularly a mammalian cell, more particularly a mammalian T-lymphocyte is provided, comprising i. the chimeric antigen-receptor polypeptide according to the first aspect of the invention, and
ii. an effector function functionally linked to the chimeric antigen-receptor polypeptide heterodimer.

In certain embodiments the effector function is:

i. a reporter protein, and/or
ii. the ability to induce cell death, particularly apoptosis, in cells bound to the chimeric antigen-receptor polypeptide heterodimer.

In certain embodiments the reporter protein is selected from:

i. a fluorescent protein,
ii. a luciferase protein,
iii. an antibiotic resistance gene,
iv. a Cre recombinase,
v. a CAS-9 nuclease, or vi. a CAS-9 chimeric transcriptional suppressor or activator.

According to a seventh aspect of the invention a method for obtaining a preparation of T-lymphocytes having a reduced reactivity against an antigen is provided. The method comprises:

i. providing a preparation of T-lymphocytes obtained from a patient,
ii. contacting the preparation of T-lymphocytes with mammalian cells according to the fifth or sixth aspect of the invention, wherein the mammalian cell is characterized in that the effector function is able to induce cell death, particularly apoptosis, in cells bound to the chimeric antigen-receptor polypeptide heterodimer.

In other words, specific T lymphocytes able to bind to the oligopeptide sequences provided within the chimeric antigen-receptor polypeptide heterodimer of the mammalian cell would undergo cell death, particularly apoptosis.

According to an eighth aspect of the invention a method for depletion of T lymphocytes having an activity against specific antigens for use in a patient in need thereof is provided. The method comprises the steps of:

i. providing a preparation of mammalian cells according to the fourth aspect of the invention,
ii. administering of the mammalian cells to a patient, wherein the mammalian cell is characterized in that the effector function is able to induce cell death, particularly apoptosis, of cells bound to the chimeric antigen-receptor polypeptide heterodimer.

In other words T lymphocytes able to bind to the oligopeptide sequence that is displayed in the chimeric antigen-receptor polypeptide heterodimer are selectively depleted. This can be used for example for the reduction or removal of autoreactive T lymphocytes in a patient with need thereof.

In certain embodiments this method is used to treat autoimmune diseases such as allergies. In certain embodiments this method is used for the prevention and treatment of organ rejection after transplantation.

According to a ninth aspect of the invention, a mammalian cell according to the fourth aspect of the invention is provided for use in the treatment or prevention of autoimmune disease, transplant rejection or immune dysfunction including but not limited to, type 1 diabetes, multiple sclerosis, rheumatoid arthritis, Crohn's disease and inflammatory bowel syndrome. In other words, the mammalian cell is used for the depletion of T-lymphocytes having an activity against specific, disease associated antigens.

According to a tenth aspect of the invention a method for detecting a patient's immune response to an oligopeptide is provided. The method comprises the steps of:

i. providing the mammalian cell according to the fourth aspect of the invention, wherein said cell comprises a reporter protein functionally linked to said chimeric antigen-receptor polypeptide heterodimer,
ii. providing a blood sample of the patient ex-vivo containing T lymphocytes involved in the immune response,
iii. contacting the mammalian cell with the blood sample under conditions allowing for the effector function to operate, and
iv. detecting the reporter protein in the mammalian cell.

In other words if in the blood of an individual T lymphocytes able to bind to the used oligopeptide are enriched resulting in a strong reporter protein expression this indicates an immune response against the oligopeptide.

In certain embodiments the oligopeptide used in this method is derived from a virus, a bacterium, a fungus or a parasite.

In certain embodiments the method according to the ninth aspect of the invention further comprises the steps of i. separating the mammalian cells according to the expression of the reporter protein,
ii. isolating DNA from the separated mammalian cells, and
iii. sequencing of the oligopeptide, encoded in the chimeric antigen-receptor polypeptide heterodimer according to the first aspect of the invention.

In other words a multitude of the mammalian cells according to the fourth aspect of the invention with different oligopeptides in the chimeric antigen-receptor polypeptide heterodimer is used. Each of these oligopeptides is derived from a certain pathogen, allergen, tumour or inflamed tissue (in the case of an autoimmune patient). This allows simultaneous testing for a multitude of different immune responses. One non-limiting example is the use as a diagnostic tool.

Wherever alternatives for single separable features such as, for example, a linker sequence, linker length, are laid out herein as "embodiments", it is to be understood that such alternatives may be combined freely to form discrete embodiments of the invention disclosed herein. The person skilled in the art understands that isolated features of the invention mentioned as specific embodiments may be combined with any other features mentioned.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows structure and antigen-specific reactivity of the MCR2 sensor (chimeric antigen-receptor polypeptide heterodimer with extracellular parts from MHC II). (a) Schematic representation of the MCR2 and its interaction with the peptide-specific TCR. (b) Surface expression of the MCR2(gp61) on BEKO thymoma cells (c) Time course of MCR2(gp61) (left panel) or MCR2(OVA) (right panel) down-regulation in BEKO cells co-cultured with gp61-specific Smarta or OVA-specific OT-II TCR transgenic CD4+T-cells. Values show MCR2 levels depicted as percentage of mean fluorescence intensity at the start of co-culture. (d) Time course of peptide-specific NFAT activation (GFP expression) in H18.3.13 cells transduced with MCR2 (gp61) or MCR2(OVA) co-cultured with Smarta or OT-II CD4+T-cells. Histogram shows examples of NFAT activation measurements in MCR2(gp61)+ cells at indicated time points. (e) Sensitivity of peptide-specific reporter cells. MCR2(gp61)+ H18.3.13 cells were diluted in MCR2 (OVA)+ H18.3.13 cells and NFAT activation was measured in untreated cells (triangles) or after co-cultured with Smarta CD4+T-cells (squares). The graph shows a linear ($R>0.99$) correlation between the percentage of GFP+ H18.3.13 cells and the percentage of cells carrying the MCR2(gp61) (f) Minimal frequency of peptide-specific T-cells able to trigger robust NFAT activation in MCR2+ reporter cells. Splenocytes from Smarta and OT-II transgenic mice were mixed at different ratios and used to stimulate MCR2(gp61)+ or MCR2(OVA)+ H18.3.13 cells. The graph shows percentage of GFP+ cells among MCR2(gp61)+ H18.3.13 or MCR2 (OVA)+ H18.3.13 cells as a function of the percentage of peptide-specific CD4+T-cells, after 8 h of co-culture. (g) The minimal number of peptide-specific T cells able to trigger a response in reporter cells. NFAT activation in MCR2(gp61)+ (left) and MCR2(OVA)+(right) H18.3.13 cells following overnight co-culture with different numbers of Smarta or OT-II CD4+T-cells. h) Kinetics of LCMV-specific CD4+T-cell expansion in the blood of infected mice (n=3) detected by the activation of MCR2(gp61)+ H18.3.13 cells. Percentage of GFP+ reporter cells after overnight co-culture with blood taken at different days post infection is shown. Blood from a naïve Smarta mouse was used as a positive control.

FIG. 2 shows screening for gp61 mimotopes. (a) A scheme of RAG-mediated peptide randomization based on which the MCR2(gp61-RSS) mimotope library was generated (see materials and methods), RSS—recombination signal sequence. (b) Examples of altered gp61 sequences found in the library (new amino acids are shown in grey). (c) 16.2c11 cells carrying the NFAT-FT reporter were transduced with the MCR2(gp61-RSS) library or with MCR2 (OVA) or MCR2(gp61) as controls and co-cultured with Smarta or OT-II CD4+T-cells hybridomas. Single MCR2 (gp61-RSS)+ cells showing NFAT activation (blue-FT fluorescence) after 9 h co-culture with the gp61-specific Smarta hybridoma (top right panel) were sorted and expanded. (d) Activation of MCR2(gp61)+, MCR2(gp61S)+ and MCR2 (gp61N)+ 16.2c11 cells co-cultured with the Smarta hybridoma. (e) Sequences of the original gp61 and two new gp61 mimotopes found in the MCR2(gp61-RSS) library. (f) CFSE dilution in Smarta CD4+T-cells after a 3-day co-culture with dendritic cells pulsed with gp61 mimotopes at different concentrations (histograms) and cytokine production at a concentration of 100 nM (dot plots).

Figure 3D:
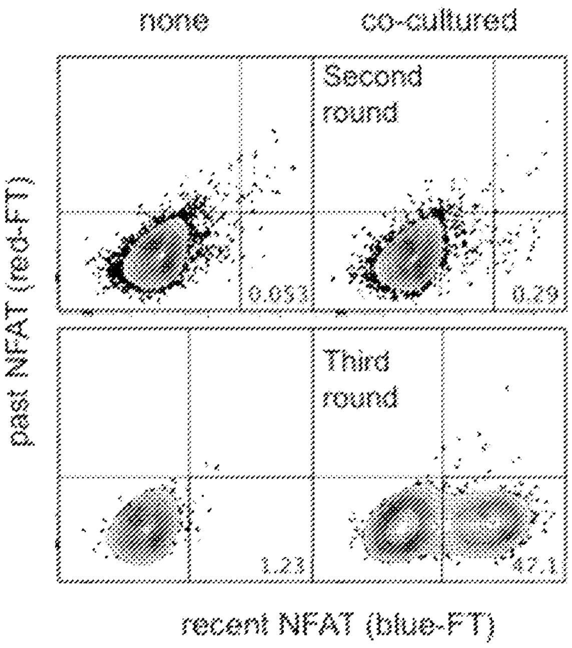
Figure 3E:
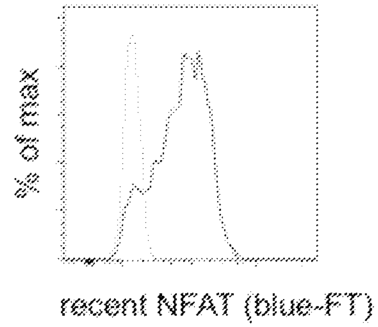

FIG. 3 shows search for new LCMV epitopes. (a, b) CD4+ T-cells from mice infected with LCMV were purified from the spleens 5 and 8 days p.i. and fused with BW5147 cells carrying an NFAT-GFP reporter. Reactivity of the resulting hybridomas was determined by GFP expression after co-culture with LCMV- or gp61-pulsed dendritic cells. Histograms (a) show examples of different types of reactivity (LCMV-open or gp61-filled dark grey) and the table (b) a summary of the data (c) A scheme of the cloning strategy for the construction of libraries enriched for naturally occurring peptides (NPLs). ORF—open reading frame dictating the natural protein sequence (d) MCR2(LCMV-NPL)+ 16.2c11 reporter cells were co-cultured with LCMV-reactive hybridomas (H2, H3, H14 and H30) of unknown peptide-specificity. Activated reporter cells were sorted, expanded and co-cultured again with the corresponding hybridomas. To achieve enough enrichment this procedure was repeated three times. Dot plots show example NFAT-activation after two or three rounds of co-culture. (e) After the 3rd round of enrichment, single cells were sorted, expanded and their reactivity verified by co-culture with hybridomas (histogram shows example NFAT reactivity). The table on the right shows frequencies of reactive clones. Peptide sequences from the MCR2 constructs, representing the dominant NP311 epitope and the new NP547 epitope are shown below.

Figure 4:
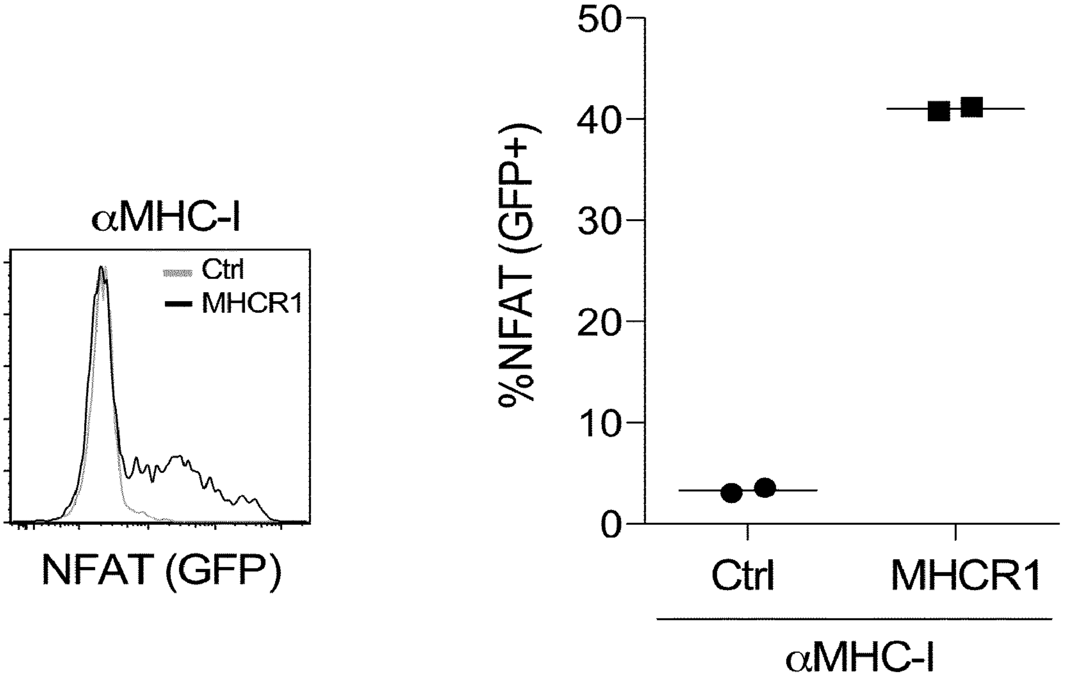

FIG. 4 shows a function test of the MCR1 (chimeric antigen-receptor polypeptide heterodimer with extracellular parts from MHC I; gp33/H2-Kb) molecule transduced into the H18.3.13 reporter cell line. (A) After an over-night culture in wells coated with αMHC-I antibodies NFAT activation was induced in the MCR1-transduced, but not in control cells.

Figure 5A:
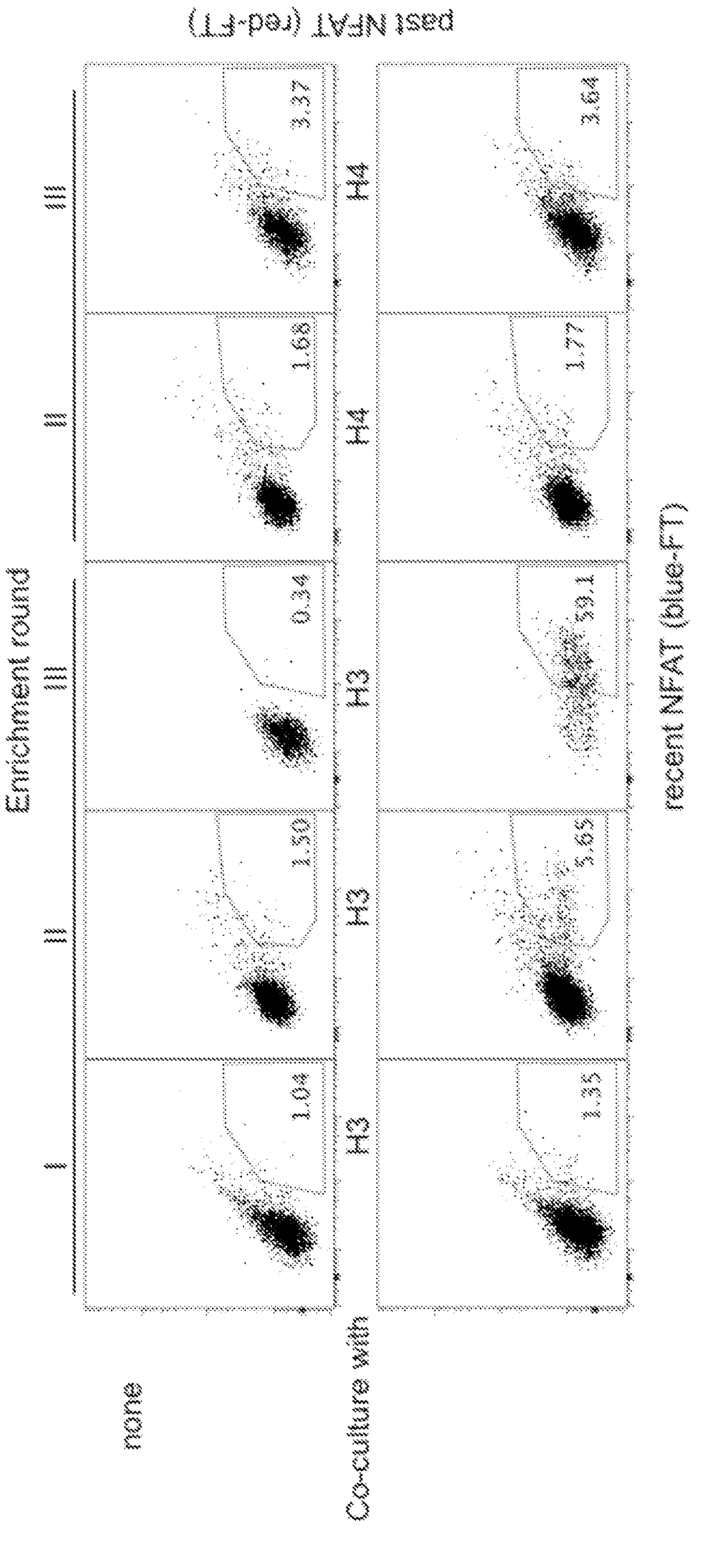
Figure 5B:
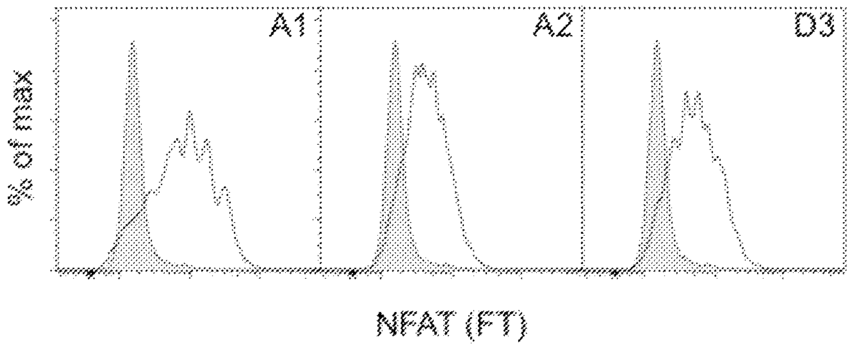

FIG. 5 shows a) Activation of MCR2(LCMV-NPL)+ 16.2c11 cells after one, two and three rounds of enrichment by co-culture with hybridomas H3 and H4. b) Examples of activation of MCR2+ 16.2c11 clones derived from the screening of a random peptide MCR2 library with the hybridoma H9 after the final co-culture. Examples of sequences recovered from the library before and after enrichment for H9-reactive peptides are shown.

Figure 6A:
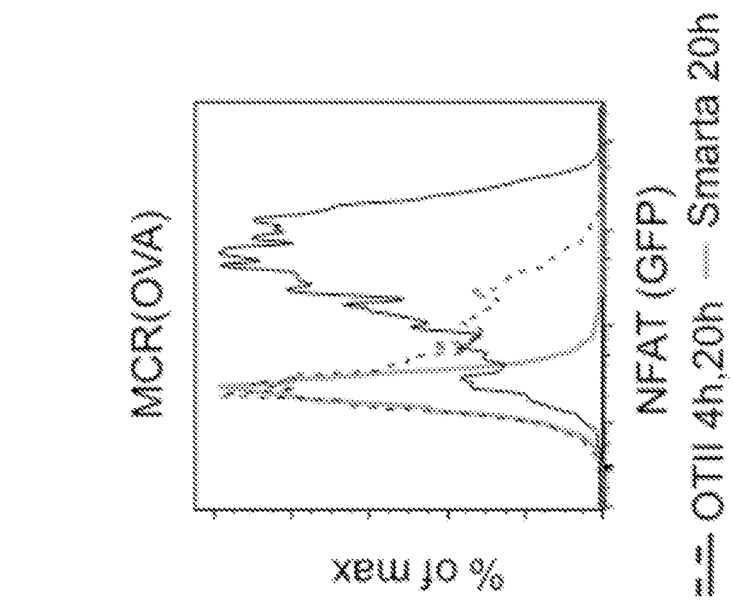
Figure 6B:
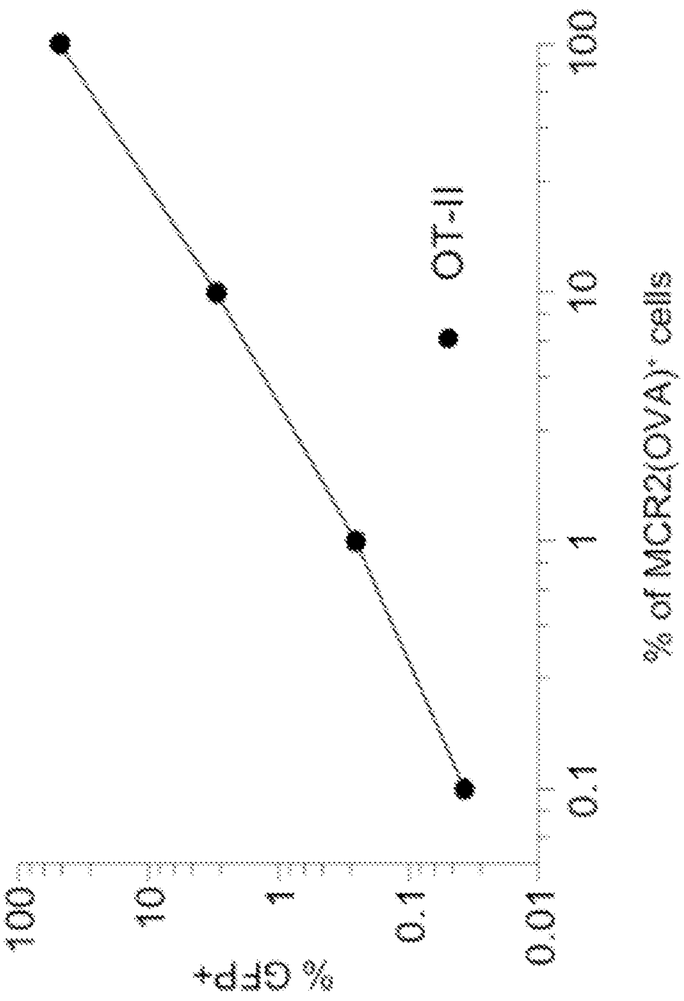

FIG. 6 shows peptide-specific reactivity and sensitivity of the MCR2 sensor. a) Time course of peptide-specific NFAT activation (GFP reporter expression) in MCR2(OVA)+ H18.3.13 cells co-cultured with OT-II CD4+T-cells or Smarta CD4+T-cells as controls. Histogram shows examples of NFAT-activation measurements in MCR2(OVA)+ cells at indicated time points b) Sensitivity of peptide-specific reporter cells. MCR2(OVA)+ H18.3.13 cells were diluted in MCR2(gp61)+ H18.3.13 cells and NFAT activation was measured after co-culture with OT-II CD4+T-cells. The graph shows a linear (R>0.99) correlation between the percentage of GFP+ H18.3.13 cells and the percentage of cells carrying the MCR2(OVA).

EXAMPLES

Example 1: Screening of T-Cell Epitopes in Mammalian Cells Using the Disclosed Chimeric Antigen-Receptor Polypeptide Heterodimer Current methods to identify cognate T-cell epitopes are based in principle on two major approaches. The first approach relies on detecting physical MHC-TCR interactions by staining T-cells with MHC-tetramers or by staining phage, yeast or insect cells displaying peptide-MHC complexes with recombinant TCRs. The second approach relies on measuring T-cell activation in co-cultures with dendritic cells (DCs) presenting peptide pools or positional scanning combinatorial peptide libraries. Screening of MHC-tetramer libraries is effective for defining the fine-specificity of recognition of known or predicted antigens, but because not all peptide-MHC tetramers bind with equal strength, low affinity interactions may be easily missed (e.g. 400 times more OVA-I-$A^b$ tetramers than gp66-I-$A^b$ tetramers are needed, for similar staining of OVA-specific OT-II and gp61-specific Smarta2 T-cells, respectively). Similar affinity constraints apply to current peptide-MHC display methods, were soluble TCRs are used. Furthermore, MHC molecules have to be mutagenized to allow efficient surface expression on phages or yeast cells. Screening of positional scanning combinatorial peptide libraries takes advantage of the cross-reactivity of the TCR and uses peptide pools to define motifs that lead to T-cell activation. While T-cell epitopes resembling naturally occurring peptides have been found with this method, the identified peptides often have no clear homology to known proteins and one need to resort to bioinformatics approaches.

The inventors disclose herein the development of an universal system that allows direct, unbiased, sensitive and efficient epitope screening in mammalian cells. Such a method should: i) provide a complex mixture of APCs, each presenting peptides of one, unique, naturally occurring sequence; ii) provide efficient means to identify and separate APCs presenting cognate peptides; iii) offer a possibility to iteratively repeat the procedure and iv) allow easy recovery of peptide sequences by cloning. To generate APCs fulfilling the first criteria, the inventors followed the approaches used to produce "single-peptide" mice and to construct different peptide-MHC display systems. By means of recombinant DNA technology a peptide was attached directly to the MHC molecule, making a stable complex and preventing other peptides from binding. A library of such peptide-MHC complexes transfected into MHC-deficient cells yields a pool of cells each presenting a unique peptide (for details see Materials and Methods). Ideally, identification of APCs carrying cognate peptides for particular T-cells would involve an easily measurable signal once their peptide-MHC complexes were bound by the TCRs of the specific T-cells. Therefore the peptide-MHC fusion molecule was linked to the TCR complex, which is tailor-made for sensing low-affinity interactions. Direct zeta chain (CD247) fusions have been successfully used to construct various chimeric antigen receptors. However, to create a molecular sensor resembling the native TCR complex as close as possible, the peptide MHC complexes were fused to truncated TCRα and TCRβ chains consisting of the hinge region, trans-membrane (TM) and intracellular (IC) domains. Connecting the peptide-MHC to the whole TCR signaling machinery provides more physiological signals. This MHC-TCR chimera is referred to as the MCR in the context of this specification. Such a molecule, upon transfection into TCR-deficient T-cell hybridomas, allows direct monitoring of peptide-MHC engagement by the TCRs of specific T-cells using an NFAT-EGFP reporter system (FIG. 1*a*). Co-culture of cells carrying a library of peptide-MCR molecules with antigen-specific T cell clones or hybridomas allows direct identification of cognate peptide specificities of T-cells by massively parallel, functional screening in mammalian cells.

Therefore the MCR was designed and cloned for the screening of cognate peptides of MHC class II-restricted T-cells, hence MCR2. MCR2 consists of two chains: the α-chain, composed of the extracellular domains of the I-$A^b$ MHC class II α-chain linked to a truncated TCRα; and the β-chain composed of a peptide (the dominant LCMV-derived epitope, gp61) and the extracellular domains of the I-$A^b$ MHC class II β-chain linked to a truncated TCRβ (FIG. 1*a*). A second MCR2 was also cloned carrying the OVA-peptide and the two were designated MCR2(gp61) and MCR2(OVA), respectively. After transduction of the MCRs into a MHC-$II^-$$TCR^-$ BEKO thymoma cell line, their expression was verified by staining with anti-MHC-II antibodies. As depicted in FIG. 1*b*, the MCR2 was efficiently expressed on the cell surface, indicating that it assembled with CD3 components of the TCR complex. To verify its specificity, BEKO cells expressing MCR2(gp61) or MCR2 (OVA) were co-cultured, with purified Smarta2 or OT-II $CD4^+$ T-cells. A very fast, peptide-specific MCR2 down-regulation from the surface was observed, with kinetics identical to conventional TCRs. MCR2(gp61) was down-regulated in co-cultures with Smarta2 T-cells and not in the presence of OT-II T-cells (FIG. 1*c*, left panel). The reverse was true for the MCR2(OVA), highlighting the specificity of the MCR2 system (FIG. 1*c*, right panel). We further assessed the ability of the MCR2 to trigger NFAT activation by transducing it into a TCR-deficient T-cell hybridoma carrying the NFAT-EGFP reporter (H18.3.13). Again, NFAT response was only triggered when MCR2-carrying hybridomas were co-cultured with peptide-specific T-cells (FIG. 1*d*). The response was robust and easily measurable already after 2 h (FIG. 1*d* most right panel).

The inventors tested the sensitivity of the MCR system by mixing $MCR2(gp61)^+$ and $MCR2(OVA)^+$ reporter cells at different ratios and measuring NFAT-activation after co-culture with Smarta2 or OT-II $CD4^+$ T-cells. As shown in FIG. 1*e*, it was possible to directly detect specific NFAT-reporter expression in cells present at frequencies above 1/10000. Importantly, a linear correlation between the percentage of detected NFAT-EGFP expressing cells and the percentage of cells carrying the "T-cell/idotype-specific" MCR2 was observed, indicating that specific cells present at frequencies lower than 1/10000 are still NFAT-EGFP', even if they cannot be distinguished from the background. The lowest frequency of peptide specific T-cells in a heterogeneous population, that was able to trigger robust NFAT-activation in $MCR2^+$ cells was also determined. Sorted $CD4^+$ T-cells (FIG. 1*f*, top panel) or unsorted splenocytes (FIG. 1*f*, bottom panel) from Smarta2 and OT-II mice were mixed at different ratios and used to stimulate $MCR2(gp61)^+$ or $MCR2(OVA)^+$ cells. Even with only 1% peptide-specific $CD4^+$ T-cells, 50% of the maximal NFAT-activation was triggered in $MCR2^+$ cells, when T-cells were provided in excess. Remarkably, as shown in FIG. 1*g* (left panel), even a single Smarta2 $CD4^+$ T-cell was able to trigger significant NFAT-EGFP activation in $MCR2(gp61)^+$ cells, while in the case of $MCR2(OVA)^+$ cells, 5 cells were required, probably due to a lower interaction affinity (FIG. 1*g* right panel). These results indicate that the MCR-technology can be used as a sensitive diagnostic tool for monitoring T cell specificities in the blood taken from patients. Indeed MCR2 $(gp61)^+$ reporter cells can be used to efficiently track antigen-specific $CD4^+$ T-cell expansion in the blood of LCMV-infected animals (FIG. 1*h*). These results demonstrate the great sensitivity of the MCR-method.

To use the disclosed invention for finding rare specific peptides in a complex library, multiple iterative cycles of co-culture and sorting of $NFAT\text{-}EGFP^+$ reporter cells are necessary. Because efficient detection of NFAT-activation in subsequent rounds of stimulation depends on fast disappearance of NFAT-reporter signals triggered in previous rounds, the very stable EGFP was replaced with the slow Fluorescent Timer (sFT). This mutant of mCherry changes "color" with time, enabling the distinction of recent (blue-mCherry) and past NFAT-activation (red-mCherry) and therefore allows for much shorter intervals between subsequent rounds of stimulation.

Figure 2A:
Figure 2B:
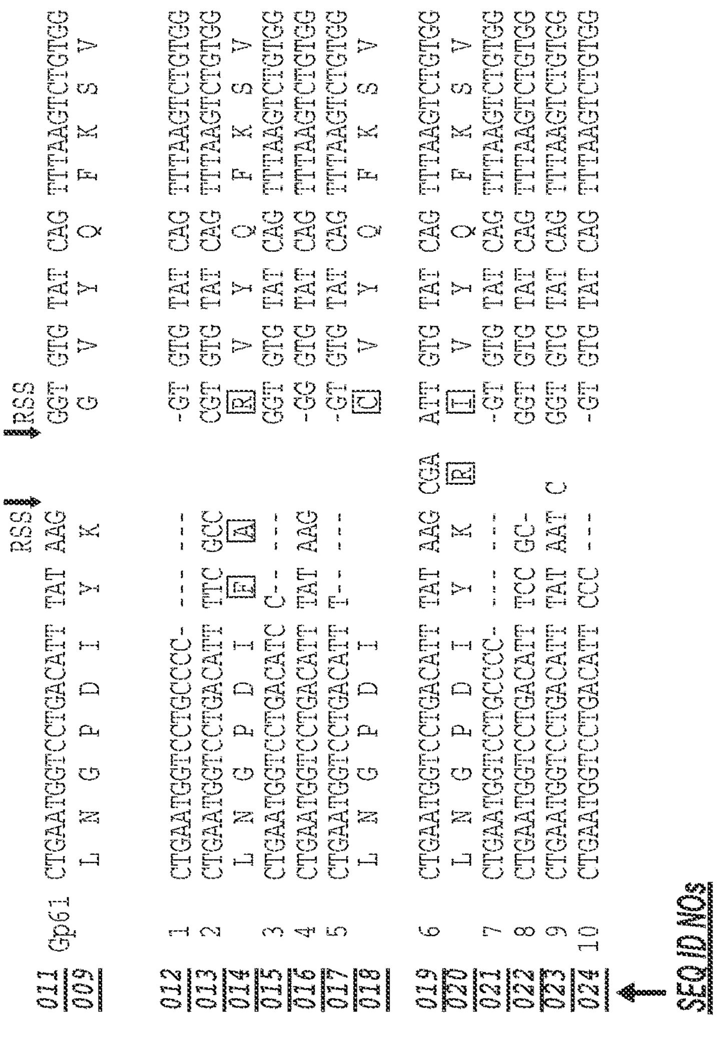
Figure 2C:
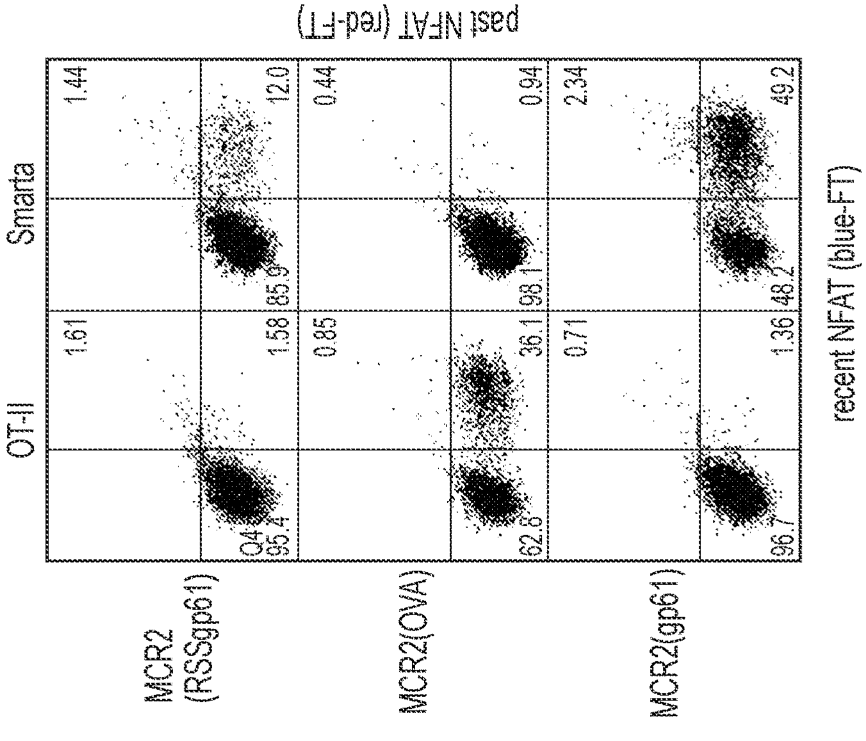
Figure 2D:
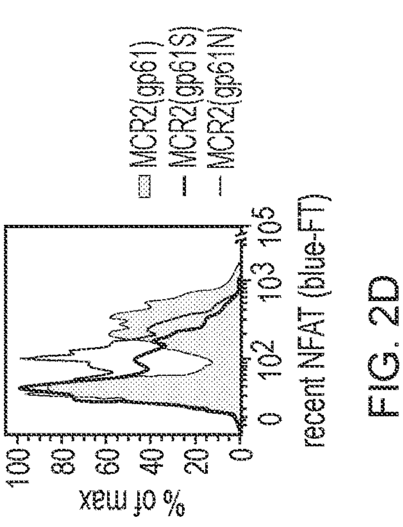
Figure 2E:
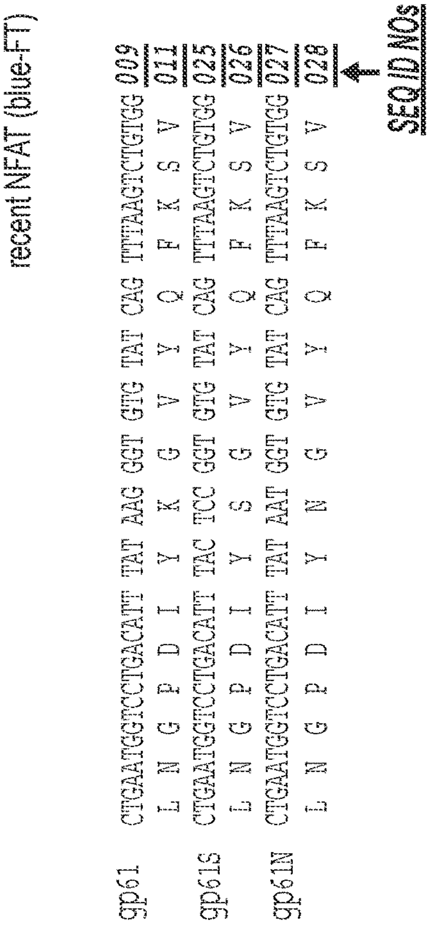
Figure 2F:
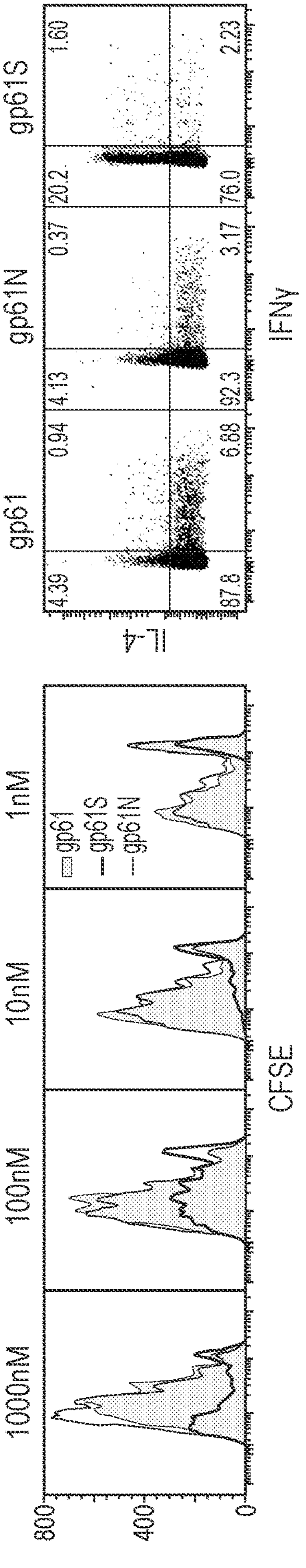

First the disclosed invention was applied to search for mimotopes of gp61 in the MCR2(gp61-RSS) library, generated by randomizing center residues of gp61 through RAG-mediated rearrangement (FIG. 2*a* and M&M). Randomly picked clones consistently contained unique mutants of the gp61-sequence (FIG. 2*a*). After transducing this library into NFAT-sFT carrying reporter cells (16.2c11), $MCR2^+$ cells were sorted, expanded and co-cultured with gp61-specific or OVA-specific T-cell hybridomas (FIG. 2*b*). Around 10% of the MCR2(gp61-RSS/I-$A^b$)$^+$16.2c11 cells showed blue NFAT-reporter activation when co-cultured with gp61-specific hybridomas. These cells were sorted as single cells, expanded and rescreened (FIG. 2*c*). All of the 24 tested clones responded to re-stimulation with gp61-specific hybridomas. PCR-amplification and sequencing of the peptide parts of the MCRs from these clones revealed two new mimotopes and the original gp61 peptide (FIG. 2*c*). The lysine at position 9 of gp61 was mutated to serine (gp61S) or to asparagine (gp61N), indicating that it is not absolutely required for Smarta2 T-cell activation. However, the level of NFAT-activation suggested that Smarta2 TCR binds the new mimotopes (in particular gp61S) with lower affinity (histogram in FIG. 2*c*). In co-cultures of T-cells with dendritic cells, both mimotopes induced robust Smarta2 T-cell responses. Interestingly, while gp61N induced proliferation and Th1-like cytokine production similarly to the original peptide, the suboptimal gp61S was much less efficient in driving proliferation, but induced a strong Th2-like cytokine response (FIG. 2*d*).

Finally, a screen for novel LCMV epitopes with the help of $CD4^+$ T-cell hybridomas derived from LCMV-infected animals 5 and 8 days post infection was performed (FIGS. 3*a* and *b*). The hybridomas carried an NFAT-EGFP reporter that allowed verification of their reactivity against LCMV and pick gp61-nonreactive hybridomas for further analysis (FIG. 3*b*). Five such hybridomas (H30, H14, H2 responding strongly and H4, H3 responding weekly) were used to screen 16.2c11 reporter cells transduced with a library of MCR2 molecules carrying all possible, overlapping peptides of the LCMV glycoprotein (GP) and nuclear protein (NP). This "genuine peptide library" (GPL) was generated by cloning random pieces of cDNA encoding GP and NP into the MCR2 vector (FIG. 3*c*) and has a significant advantage over random or combinatorial peptide libraries, as many (⅙) of the recovered peptides represent native proteins. Indeed, for 4 out of 5 hybridomas, the LCMV-specific target peptides were directly identified. Three of the hybridomas (H30, H14 and H2) recognized a known dominant LCMV-epitope NP311 and H3 reacted with a new epitope NP547 (FIG. 3*d*). The fifth hybridoma (H4) did not yield any enrichment for reactive reporter cells even after 3 iterative rounds of screening. TCR surface expression was tested on this hybridoma and was found to be TCR-negative. The TCR was probably lost during expansion after the initial LCMV-specificity screening. This result further verifies the TCR-specificity of the disclosed method. One additional hybridoma (H9) was used to screen a MCR2 library carrying random peptides and found several strongly reactive epitopes, but they did not resemble any LCMV peptides. This further supports the strategy of using GPLs rather than random peptide libraries for T-cell epitope screening.

Herein a new molecular sensor is disclosed, which allows for sensing of peptide-MHC-TCR interactions on the APC side with great specificity, sensitivity and fast kinetics. Using this reporter, a novel approach for unbiased, functional screening of T-cell epitopes was established. It combines the versatility of expression cloning with the sensitivity and high-throughput capabilities of fluorescence activated cell sorting and allows for efficient iterative screening of peptide libraries in mammalian cells. All this provides significant advantages over the methods known in the art. First, thanks to the multivalent interaction between the MCRs and TCRs, high and low affinity binding generate similar NFAT-reporter signals (FIG. 1*d*) and therefore low affinity ligands are less likely to be missed. Indeed, even though LCMV epitopes have been extensively studied, a novel epitope—NP547 could be identified. Second, engineering of individual recombinant TCRs or mutagenesis of the MHC are not required, as the peptides are screened in the context of native TCR and MHC molecules expressed on the surface of mammalian cells. Third, as exemplified by the LCMV virus peptide screen, the MCR-technology facilitates efficient screening of libraries highly enriched for peptides derived from the pathogen/cell/tissue targeted by the T-cell of interest.

The MCR-based approach provides a versatile, easy to use and powerful way of identifying antigenic specificities of T-cells. As such, it may impact several fields of basic and clinical research. Defining specificities of regulatory and effector tumour-infiltrating T-cells enables the discovery of novel tumour-antigens. Defining the specificities of autoreactive tissue-infiltrating T-cells aids in the development of antigen-specific therapies for autoimmune diseases. In this respect, MCR may also allow for efficient redirecting of T-cell effector functions towards peptide-specific T-cells, enabling the purging of the repertoire from undesired specificities. Furthermore, screening of mimotope libraries will lead to the discovery of high affinity peptide variants and the development of sensitive flow cytometry based tests for antigenic reactivity of T-cells circulating in the blood of patients.

Materials and Methods

Mice

C57/Bl6, mice were purchased from Charles River. Smarta2 and OT-II mice were bred at the ETH mouse facility.

Cell Lines

Beko is a spontaneous thymoma cell line derived from TCRβ-deficient mice. The H18.3.13 reporter cell line was generated by retrovirally transducing the NFAT-EGFP reporter (carrying four copies of the minimal human IL-2 promoter, each containing 3 NFAT binding sites ACGCCTTCTGTATGAAACAGTTTTTCCTCC (SEQ ID NO 001), inserted upstream of the EGFP coding sequence) into a $TCR^-$ B6 T-cell hybridoma. The 16.2c11 reporter cell line was generated by transfecting the 16.2 T-cell hybridoma with the NFAT-sFT reporter construct and a vector encoding the murine eco-tropic retrovirus receptor Slc7a1.

Hybridoma Generation

Sorted T-cells or thymocytes were activated with plastic-bound anti-CD3ε and anti-CD28 antibodies in the presence of mouse IL-2 for 2-3 days. Equal numbers of activated T-cells and the $TCR\alpha^-\beta^-$ BW5147 fusion partner were fused using PEG-1500, and plated at limiting dilution in the presence of 100 mM hypoxanthine, 400 nM aminopterin, and 16 mM thymidine (HAT).

Cloning of the MCR2

The MCR2 α and β chains were cloned by standard techniques and contain the following parts:

MCR2 α chain: the MHC-II I-$A^b$ α chain residues 1-208 linked to the TCRα chain constant region residues 87-137 by the GGSGGSAQ (SEQ ID NO 002) linker.

MCR2 β chain: the MHC-II I-$A^b$β chain residues 1-217 linked to the TCRβ chain constant region (C1) residues 123-173 by the AQSGGSGGSAQ (SEQ ID NO 003) linker. In the MCR2(gp61) residues DS at positions 29 and 30 of the MHC-II part were replaced by the amino acid sequence

```
SGLNGPDIYKGVYQFKSVGSGGSGGSGDS (SEQ ID NO 004;
containing the gp61 peptide).
```

In MCR2(OVA) the same residues were replaced by the amino acid sequence

```
SISQAVHAAHAEINEAGRGSGGSGGSGDS (SEQ ID NO 005;
containing the OVA peptide).
```

Retro Viral Transduction of Reporter Cell Lines and Sorted Thymocytes

MCRα and MCRβ were cloned into the pMYiresGFP retroviral vector, so that MCRβ replaced GFP. Throughout the study we used this vector (pMY-MCRαiresMCRβ) to generate MCRs containing various peptides and referred to them as MCR ("peptide"/"MHC haplotype"). Retrovirus containing supernatants were produced in the ecotropic Phoenix packaging cell line and used to infect reporter cell lines and sorted cells.

RAG-Mediated Generation of Mimotope Libraries

To generate the gp61 mimotope library, the MCR2(gp61-RSS-EGFP-RSS/I-$A^b$) construct was built by inserting a stuffer fragment containing EGFP and the RAG recombination signal sequences (RSS) into the middle of the gp61 peptide in the MCR2(gp61) construct (FIG. 2*a*). This construct was transduced into sorted $CD4^-CD8^-$ double-negative (DN) thymocytes cultured on Tst-4/DLL1[32]. After a week of culture (during which DN cells develop into $CD4^+$ $CD8^+$ double-positive (DP) cells and recombine their TCR genes, as well as the RSS-EGFP-RSS stuffer, by RAG-mediated rearrangement) cells expressing low levels of EGFP were sorted and cDNA was made. The peptide-encoding part of the recombined MCR2(gp61-RSS-EGFP-RSS/I-$A^b$) construct was PCR amplified from the cDNA and cloned into the empty MCR2(I-$A^b$) vector, generating the MCR2(gp61-RSS/I-$A^b$) mimotope library.

Genuine and Random Peptide Library Generation and Screening

To generate the MCR2-LCMV genuine overlapping peptide library DNA encoding the GP and NP proteins was digested for a limited amount of time (Takara DNA fragmentation Kit). The fragments were ligated with linkers homologous to vector sequences flanking the cloning site, PCR amplified, cloned into the pMY-MCR2 vector by Gibsson assembly and transfected into bacteria generating over 2*$10^6$ clones. 16.2c11 cells were transduced with this library and 0.5*$10^6$ $MCR^{low}$ and 2.2*$10^4$ $MCR^{hi}$ cells were sorted.

The MCR2 random peptide library was made by cloning an oligonucleotide (GGTNNNNNNTWCNNNNNNBCCNNN-SCCNNNNNNKCCNNNGGA) (SEQ ID NO 006) into the MCR2-vector using the strategy described above. This oligonucleotide encoded random amino acids at positions facing the TCR, while anchor residues were partially fixed to ensure good presentation. The complexity was 5.5*$10^6$ bacterial clones and after transduction 11.5*$10^6$ individual MCR2+ cells were sorted.

MCR Down-Regulation Assay

If not stated otherwise, $MCR2^+$ Beko cells were co-cultured with a 5-fold excess of sorted $CD4^+$ T-cells from indicated donor mice.

Stimulation of $MCR^+$ H18.3.13 or 16.2c11 Cells

If not stated otherwise, $MCR2^+$ cells were co-cultured with a 5-fold excess of sorted $CD4^+$ T-cells or $CD4^+$ T-cell hybridomas from indicated donor mice for 8-12 h.

Example 2: Chimeric Antigen-Receptor Polypeptide Heterodimer

```
First polypeptide, alpha chain (SEQ ID NO 007):
MPRSRALILGVLALTTMLSLCGGEDDIEADHVGTYGISVYQSPGDIGQY

TFEFDGDELFYVDLDKKETVWMLPEFGQLASFDPQGGLQNIAVVKHNLG

VLTKRSNSTPATNEAPQATVFPKSPVLLGQPNTLICFVDNIFPPVINIT

WLRNSKSVADGVYETSFFVNRDYSFHKLSYLTFIPSDDDIYDCKVEHWG
```

-continued

```
LEEPVLKHWEPEGGSGGSAQSDVPCDATLTEKSFETDMNLNFQNLSVMG

LRILLLKVAGFNLLMTLRLWSS
```

Amino acids 1-208 are derived from MHC2 alpha. Amino acids 209-216 are a linker sequence. Amino acids 217-267 are derived from TCR alpha.

```
Second polypeptide, beta chain (SEQ ID NO 008):
MALQIPSLLLSAAVVVLMVLSSPRTEGGSGGSGGSGDSERHFVYQFMGE

CYFTNGTQRIRYVTRYIYNREEYVRYDSDVGEHRAVTELGRPDAEYWNS

QPEILERTRAELDTVCRHNYEGPETHTSLRRLEQPNVVISLSRTEALNH

HNTLVCSVTDFYPAKIKVRWFRNGQEETVGVSSTQLIRNGDWTFQVLVM

LEMTPRRGEVYTCHVEHPSLKSPITVEWRAQSGGSGGSAQGRADCGITS

ASYQQGVLSATILYEILLGKATLYAVLVSTLVVMAMVKRKNS
```

Amino acids 1 to 26 are a leader peptide. Between amino acids 27 and 28 is the insertion site of oligopeptides to be displayed. Amino acids 29 to 36 are a linker sequence. Amino acids 37 to 228 are derived from MHC2 beta. Amino acids 229 to 236 are a linker sequence. Amino acids 237 to 287 are derived from TCRbeta.

Peptides to be inserted in SEQ ID NO 008 between amino acids 27 and 28 (GG):

```
Gp61 (SEQ ID NO 009):
LNGPDIYKGVYQFKSV

OVA (SEQ ID NO 010):
ISQAVHAAHAEINEAGR
```

The invention claimed is:

1. A method for the identification of a TCR recognizable peptide sequence, comprising:

i. providing a plurality of mammalian cells, wherein each of said plurality of mammalian cells expresses a member of a library;

each member of said library encodes a transgenic antigen receptor;

said transgenic antigen receptor comprises an oligopeptide different for each member of the library and a chimeric antigen-receptor polypeptide heterodimer comprising a first polypeptide and a second polypeptide, wherein:

a. said first polypeptide comprises an extracellular part of a major histocompatibility complex I (MHC class I) alpha chain, wherein the oligopeptide is comprised within said extracellular part of the MHC class I alpha chain and presented in a way suitable for the recognition by a T cell receptor, and wherein said extracellular part of the MHC alpha chain retains the ability to interact with the oligopeptide and with CD8, and said second polypeptide comprises a β2-microglobulin domain, or b. said first polypeptide comprises an extracellular part of a major histocompatibility complex II (MHC class II) alpha chain and said second polypeptide comprises an extracellular part of a MHC class II beta chain, wherein the oligopeptide is comprised within said extracellular parts of the MHC class II alpha and beta chains and presented in a way suitable for the recognition by a T cell receptor, and wherein said extracellular parts of the MHC alpha and beta chains retain the ability to interact with the oligopeptide and CD4, one of said first polypeptide and said second polypeptide further comprises a hinge region, a transmembrane domain and an intracellular domain or intracellular tail of a T cell receptor alpha chain and the other one of said first polypeptide and said second polypeptide comprises a hinge region, a transmembrane domain and an intracellular domain of a T cell receptor beta chain;

said transgenic antigen receptor is functionally linked to a reporter gene, whereby binding of a cognate T cell receptor to said transgenic antigen receptor results in the activation of a reporter protein encoded by said reporter gene, ii. contacting said plurality of mammalian cells with a preparation of T-lymphocytes, iii. separating cells showing a detectable reporter protein from said plurality of mammalian cells according to the detectable level of said reporter protein, yielding activated cells, iv. isolating DNA from said activated cells, and v. sequencing of said oligopeptide sequence comprised in said transgenic antigen-receptor.

2. A method for the identification of a TCR recognizable peptide sequence, comprising:

i. providing a mammalian cell, wherein said mammalian cell expresses a transgenic antigen receptor;

said transgenic antigen receptor molecule comprises an oligopeptide and a chimeric antigen-receptor polypeptide heterodimer comprising a first polypeptide and a second polypeptide, wherein:

a. said first polypeptide comprises an extracellular part of a major histocompatibility complex I (MHC class I) alpha chain, wherein the oligopeptide is comprised within said extracellular part of the MHC class I alpha chain and presented in a way suitable for recognition by a T cell receptor, and wherein said extracellular part of the MHC alpha chain retains the ability to interact with the oligopeptide and with CD8, and said second polypeptide comprises a β2-microglobulin domain, or b. said first polypeptide comprises an extracellular part of a major histocompatibility complex II (MHC class II) alpha chain and said second polypeptide comprises an extracellular part of a MHC class II beta chain, wherein the oligopeptide is comprised within said extracellular parts of the MHC class II alpha and beta chains and presented in a way suitable for recognition by a T cell receptor, and wherein said extracellular parts of the MHC alpha and beta chains retain the ability to interact with the oligopeptide and CD4, one of said first polypeptide and said second polypeptide further comprises a hinge region, a transmembrane domain and an intracellular domain or intracellular tail of a T cell receptor alpha chain and the other one of said first polypeptide and said second polypeptide comprises a hinge region, a transmembrane domain and an intracellular domain of a T cell receptor beta chain; and said transgenic antigen receptor is functionally linked to a reporter gene, whereby binding of a cognate T cell receptor to said transgenic antigen receptor results in the activation of a reporter protein encoded by said reporter gene, ii. contacting said mammalian cell with a preparation of T-lymphocytes, thereby activating said reporter gene yielding an activated mammalian cell, iii. isolating DNA from said activated mammalian cell, and iv. sequencing of said oligopeptide sequence encoded in said transgenic chimeric antigen-receptor.

3. The method according to claim 1 or 2, wherein the oligopeptide is covalently linked to an extracellular part of the first or the second polypeptide.

4. The method according to claim 1 or 2, wherein:

(a) the extracellular part of the MHC class I alpha chain of the first polypeptide comprises an MHC class I alpha 1 domain, an MHC class I alpha 2 domain, and an MHC class I alpha 3 domain; or (b) the extracellular part of the MHC class II alpha chain of the first polypeptide comprises an MHC class II alpha 1 domain and an MHC class II alpha 2 domain, and the extracellular part of the MHC class II beta chain of the second polypeptide comprises an MHC class II beta 1 domain and an MHC class II beta 2 domain.

5. The method according to claim 4, wherein the oligopeptide sequence is inserted C-terminal to amino acid 1, 2, 3, 4, or 5 of the MHC alpha 1 domain sequence.

6. The method according to claim 1 or 2, wherein the first polypeptide comprises an amino acid sequence having at least 90% identity to SEQ ID NO: 007 and the second polypeptide comprises an amino acid sequence having at least 90% identity to SEQ ID NO: 008.

7. The method according to claim 6, wherein the first polypeptide comprises the amino acid sequence of SEQ ID NO: 007 and the second polypeptide comprises the amino acid sequence of SEQ ID NO: 008.

8. The method according to claim 1 or 2, wherein the extracellular part of the MHC class I alpha chain, the MHC class II alpha chain, and/or the MHC class II beta chain is selected from the members of the human major histocompatibility complex gene family HLA.

9. The method according to claim 1 or 2, wherein the oligopeptide is 8-40 amino acids in length.

10. The method according to claim 1 or 2, wherein the reporter protein is selected from:

i. a fluorescent protein, ii. a luciferase protein, iii. a protein encoded by an antibiotic resistance gene, iv. a Cre recombinase, v. a CAS-9 nuclease, and vi. a CAS-9 chimeric transcriptional suppressor or activator.

* * * * *

SEQUENCE LISTING

```
<160> NUMBER OF SEQ ID NOS: 45

<210> SEQ ID NO 1
<211> LENGTH: 30
<212> TYPE: DNA
<213> ORGANISM: Homo sapiens

<400> SEQUENCE: 1

acgccttctg tatgaaacag tttttcctcc                                    30


<210> SEQ ID NO 2
<211> LENGTH: 8
<212> TYPE: PRT
<213> ORGANISM: Artificial Sequence
<220> FEATURE:
<223> OTHER INFORMATION: Linker

<400> SEQUENCE: 2

Gly Gly Ser Gly Gly Ser Ala Gln
1               5


<210> SEQ ID NO 3
<211> LENGTH: 11
<212> TYPE: PRT
<213> ORGANISM: Artificial Sequence
<220> FEATURE:
<223> OTHER INFORMATION: Linker

<400> SEQUENCE: 3

Ala Gln Ser Gly Gly Ser Gly Gly Ser Ala Gln
```

-continued 1 5 10

<210> SEQ ID NO 4
<211> LENGTH: 29
<212> TYPE: PRT
<213> ORGANISM: Artificial Sequence
<220> FEATURE:
<223> OTHER INFORMATION: Synthetic construct comprising gp61 peptide
<220> FEATURE:
<221> NAME/KEY: PEPTIDE
<222> LOCATION: (3)..(18)
<223> OTHER INFORMATION: GP61 peptide

<400> SEQUENCE: 4

Ser Gly Leu Asn Gly Pro Asp Ile Tyr Lys Gly Val Tyr Gln Phe Lys
1 5 10 15

Ser Val Gly Ser Gly Gly Ser Gly Gly Ser Gly Asp Ser
20 25

<210> SEQ ID NO 5
<211> LENGTH: 29
<212> TYPE: PRT
<213> ORGANISM: Artificial Sequence
<220> FEATURE:
<223> OTHER INFORMATION: synthetic construct comprising ova peptide
<220> FEATURE:
<221> NAME/KEY: PEPTIDE
<222> LOCATION: (2)..(18)
<223> OTHER INFORMATION: OVA peptide

<400> SEQUENCE: 5

Ser Ile Ser Gln Ala Val His Ala Ala His Ala Glu Ile Asn Glu Ala
1 5 10 15

Gly Arg Gly Ser Gly Gly Ser Gly Gly Ser Gly Asp Ser
20 25

<210> SEQ ID NO 6
<211> LENGTH: 42
<212> TYPE: DNA
<213> ORGANISM: Artificial Sequence
<220> FEATURE:
<223> OTHER INFORMATION: Oligonucleotide encoding random peptides used for MCR2 library
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(33)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t

<400> SEQUENCE: 6
ggtnnnnnnt wcnnnnnnbc cnnnsccnnn nnnkccnnng ga 42

<210> SEQ ID NO 7
<211> LENGTH: 267
<212> TYPE: PRT

<213> ORGANISM: Homo sapiens
<220> FEATURE:
<221> NAME/KEY: MISC_FEATURE
<222> LOCATION: (1)..(208)
<223> OTHER INFORMATION: MHC2 alpha
<220> FEATURE:
<221> NAME/KEY: MISC_FEATURE
<222> LOCATION: (209)..(216)
<223> OTHER INFORMATION: linker sequence
<220> FEATURE:
<221> NAME/KEY: MISC_FEATURE
<222> LOCATION: (217)..(267)
<223> OTHER INFORMATION: TCR alpha

<400> SEQUENCE: 7

```
Met Pro Arg Ser Arg Ala Leu Ile Leu Gly Val Leu Ala Leu Thr Thr
1               5                   10                  15

Met Leu Ser Leu Cys Gly Gly Glu Asp Asp Ile Glu Ala Asp His Val
            20                  25                  30

Gly Thr Tyr Gly Ile Ser Val Tyr Gln Ser Pro Gly Asp Ile Gly Gln
        35                  40                  45

Tyr Thr Phe Glu Phe Asp Gly Asp Glu Leu Phe Tyr Val Asp Leu Asp
    50                  55                  60

Lys Lys Glu Thr Val Trp Met Leu Pro Glu Phe Gly Gln Leu Ala Ser
65                  70                  75                  80

Phe Asp Pro Gln Gly Gly Leu Gln Asn Ile Ala Val Val Lys His Asn
                85                  90                  95

Leu Gly Val Leu Thr Lys Arg Ser Asn Ser Thr Pro Ala Thr Asn Glu
            100                 105                 110

Ala Pro Gln Ala Thr Val Phe Pro Lys Ser Pro Val Leu Leu Gly Gln
        115                 120                 125

Pro Asn Thr Leu Ile Cys Phe Val Asp Asn Ile Phe Pro Pro Val Ile
    130                 135                 140

Asn Ile Thr Trp Leu Arg Asn Ser Lys Ser Val Ala Asp Gly Val Tyr
145                 150                 155                 160

Glu Thr Ser Phe Phe Val Asn Arg Asp Tyr Ser Phe His Lys Leu Ser
                165                 170                 175

Tyr Leu Thr Phe Ile Pro Ser Asp Asp Asp Ile Tyr Asp Cys Lys Val
            180                 185                 190

Glu His Trp Gly Leu Glu Glu Pro Val Leu Lys His Trp Glu Pro Glu
        195                 200                 205

Gly Gly Ser Gly Gly Ser Ala Gln Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
            260                 265
```

<210> SEQ ID NO 8
<211> LENGTH: 287
<212> TYPE: PRT
<213> ORGANISM: Homo sapiens
<220> FEATURE:
<221> NAME/KEY: SIGNAL
<222> LOCATION: (1)..(26)
<223> OTHER INFORMATION: leader peptide
<220> FEATURE:
<221> NAME/KEY: MISC_FEATURE
<222> LOCATION: (27)..(28)

-continued

<223> OTHER INFORMATION: insertion site of oligopeptides
<220> FEATURE:
<221> NAME/KEY: MISC_FEATURE
<222> LOCATION: (29)..(36)
<223> OTHER INFORMATION: linker sequence
<220> FEATURE:
<221> NAME/KEY: MISC_FEATURE
<222> LOCATION: (37)..(228)
<223> OTHER INFORMATION: MHC2 beta
<220> FEATURE:
<221> NAME/KEY: MISC_FEATURE
<222> LOCATION: (229)..(236)
<223> OTHER INFORMATION: linker sequence
<220> FEATURE:
<221> NAME/KEY: MISC_FEATURE
<222> LOCATION: (237)..(287)
<223> OTHER INFORMATION: TCR beta

<400> SEQUENCE: 8

```
Met Ala Leu Gln Ile Pro Ser Leu Leu Leu Ser Ala Ala Val Val Val
1               5                   10                  15

Leu Met Val Leu Ser Ser Pro Arg Thr Glu Gly Gly Ser Gly Gly Ser
            20                  25                  30

Gly Gly Ser Gly Asp Ser Glu Arg His Phe Val Tyr Gln Phe Met Gly
        35                  40                  45

Glu Cys Tyr Phe Thr Asn Gly Thr Gln Arg Ile Arg Tyr Val Thr Arg
    50                  55                  60

Tyr Ile Tyr Asn Arg Glu Glu Tyr Val Arg Tyr Asp Ser Asp Val Gly
65                  70                  75                  80

Glu His Arg Ala Val Thr Glu Leu Gly Arg Pro Asp Ala Glu Tyr Trp
                85                  90                  95

Asn Ser Gln Pro Glu Ile Leu Glu Arg Thr Arg Ala Glu Leu Asp Thr
            100                 105                 110

Val Cys Arg His Asn Tyr Glu Gly Pro Glu Thr His Thr Ser Leu Arg
        115                 120                 125

Arg Leu Glu Gln Pro Asn Val Val Ile Ser Leu Ser Arg Thr Glu Ala
    130                 135                 140

Leu Asn His His Asn Thr Leu Val Cys Ser Val Thr Asp Phe Tyr Pro
145                 150                 155                 160

Ala Lys Ile Lys Val Arg Trp Phe Arg Asn Gly Gln Glu Glu Thr Val
                165                 170                 175

Gly Val Ser Ser Thr Gln Leu Ile Arg Asn Gly Asp Trp Thr Phe Gln
            180                 185                 190

Val Leu Val Met Leu Glu Met Thr Pro Arg Arg Gly Glu Val Tyr Thr
        195                 200                 205

Cys His Val Glu His Pro Ser Leu Lys Ser Pro Ile Thr Val Glu Trp
    210                 215                 220

Arg Ala Gln Ser Gly Gly Ser Gly Gly Ser Ala Gln Gly Arg Ala Asp
225                 230                 235                 240

Cys Gly Ile Thr Ser Ala Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Thr Leu Val Val Met Ala Met Val Lys Arg Lys Asn Ser
        275                 280                 285
```

<210> SEQ ID NO 9
<211> LENGTH: 16
<212> TYPE: PRT
<213> ORGANISM: Lymphocytic choriomeningitis virus

<400> SEQUENCE: 9

Leu Asn Gly Pro Asp Ile Tyr Lys Gly Val Tyr Gln Phe Lys Ser Val
1               5                   10                  15

<210> SEQ ID NO 10
<211> LENGTH: 17
<212> TYPE: PRT
<213> ORGANISM: Gallus gallus

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 49
<212> TYPE: DNA
<213> ORGANISM: Lymphocytic choriomeningitis virus

<400> SEQUENCE: 11
ctgaatggtc ctgacattta taagggtgtg tatcagttta agtctgtgg                 49

<210> SEQ ID NO 12
<211> LENGTH: 41
<212> TYPE: DNA
<213> ORGANISM: Artificial Sequence
<220> FEATURE:
<223> OTHER INFORMATION: altered gp61 sequence

<400> SEQUENCE: 12
ctgaatggtc ctgccccgtg tgtatcagtt taagtctgtg g                         41

<210> SEQ ID NO 13
<211> LENGTH: 49
<212> TYPE: DNA
<213> ORGANISM: Artificial Sequence
<220> FEATURE:
<223> OTHER INFORMATION: altered gp61 sequence

<400> SEQUENCE: 13
ctgaatggtc ctgacatttt cgcccgtgtg tatcagttta agtctgtgg                 49

<210> SEQ ID NO 14
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 14

Leu Asn Gly Pro Asp Ile Phe Ala Arg Val Tyr Gln Phe Lys Ser Val
1               5                   10                  15

<210> SEQ ID NO 15
<211> LENGTH: 44
<212> TYPE: DNA
<213> ORGANISM: Artificial Sequence
<220> FEATURE:
<223> OTHER INFORMATION: altered gp61 sequence

<400> SEQUENCE: 15
ctgaatggtc ctgacatccg gtgtgtatca gtttaagtct gtgg                      44

-continued

<210> SEQ ID NO 16
<211> LENGTH: 48
<212> TYPE: DNA
<213> ORGANISM: Artificial Sequence
<220> FEATURE:
<223> OTHER INFORMATION: altered gp61 sequence

<400> SEQUENCE: 16
vtgaatggtc ctgacattta taaggggtgt atcagtttaa gtctgtgg 48

<210> SEQ ID NO 17
<211> LENGTH: 43
<212> TYPE: DNA
<213> ORGANISM: Artificial Sequence
<220> FEATURE:
<223> OTHER INFORMATION: altered gp61 sequence

<400> SEQUENCE: 17
ctgaatggtc ctgacatttg tgtgtatcag tttaagtctg tgg 43

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 18

Leu Asn Gly Pro Asp Ile Cys Val Tyr Gln Phe Lys Ser Val
1 5 10

<210> SEQ ID NO 19
<211> LENGTH: 52
<212> TYPE: DNA
<213> ORGANISM: Artificial Sequence
<220> FEATURE:
<223> OTHER INFORMATION: altered gp61 sequence

<400> SEQUENCE: 19
ctgaatggtc ctgacattta taagcgaatt gtgtatcagt ttaagtctgt gg 52

<210> SEQ ID NO 20
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 20

Leu Asn Gly Pro Asp Ile Tyr Lys Arg Ile Val Tyr Gln Phe Lys Ser
1 5 10 15

Val

<210> SEQ ID NO 21
<211> LENGTH: 41
<212> TYPE: DNA
<213> ORGANISM: Artificial Sequence
<220> FEATURE:
<223> OTHER INFORMATION: altered gp61 sequence

<400> SEQUENCE: 21
ctgaatggtc ctgccccgtg tgtatcagtt taagtctgtg g 41

<210> SEQ ID NO 22
<211> LENGTH: 48
<212> TYPE: DNA

-continued

<213> ORGANISM: Artificial Sequence
<220> FEATURE:
<223> OTHER INFORMATION: altered gp61 sequence

<400> SEQUENCE: 22
ctgaatggtc ctgacatttc cgcggtgtgt atcagtttaa gtctgtgg 48

<210> SEQ ID NO 23
<211> LENGTH: 50
<212> TYPE: DNA
<213> ORGANISM: Artificial Sequence
<220> FEATURE:
<223> OTHER INFORMATION: altered gp61 sequence

<400> SEQUENCE: 23
ctgaatggtc ctgacattta taatcggtgt gtatcagttt aagtctgtgg 50

<210> SEQ ID NO 24
<211> LENGTH: 45
<212> TYPE: DNA
<213> ORGANISM: Artificial Sequence
<220> FEATURE:
<223> OTHER INFORMATION: altered gp61 sequence

<400> SEQUENCE: 24
ctgaatggtc ctgacattcc cgtgtgtatc agtttaagtc tgtgg 45

<210> SEQ ID NO 25
<211> LENGTH: 49
<212> TYPE: DNA
<213> ORGANISM: Artificial Sequence
<220> FEATURE:
<223> OTHER INFORMATION: altered gp61 sequence

<400> SEQUENCE: 25
ctgaatggtc ctgacattta ctccggtgtg tatcagttta agtctgtgg 49

<210> SEQ ID NO 26
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 26

Leu Asn Gly Pro Asp Ile Tyr Ser Gly Val Tyr Gln Phe Lys Ser Val
1               5                   10                  15

<210> SEQ ID NO 27
<211> LENGTH: 49
<212> TYPE: DNA
<213> ORGANISM: Artificial Sequence
<220> FEATURE:
<223> OTHER INFORMATION: altered gp61 sequence

<400> SEQUENCE: 27
ctgaatggtc ctgacattta taatggtgtg tatcagttta agtctgtgg 49

<210> SEQ ID NO 28
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 28

Leu Asn Gly Pro Asp Ile Tyr Asn Gly Val Tyr Gln Phe Lys Ser Val
1               5                   10                  15

<210> SEQ ID NO 29
<211> LENGTH: 21
<212> TYPE: DNA
<213> ORGANISM: Artificial Sequence
<220> FEATURE:
<223> OTHER INFORMATION: example for coding sequence of random peptide

<400> SEQUENCE: 29
aacgatcgag ctgcatgcta c 21

<210> SEQ ID NO 30
<211> LENGTH: 21
<212> TYPE: DNA
<213> ORGANISM: Artificial Sequence
<220> FEATURE:
<223> OTHER INFORMATION: example for coding sequence of random peptide

<400> SEQUENCE: 30
acgatcgagc tgcatgctac a 21

<210> SEQ ID NO 31
<211> LENGTH: 21
<212> TYPE: DNA
<213> ORGANISM: Artificial Sequence
<220> FEATURE:
<223> OTHER INFORMATION: example for coding sequence of random peptide

<400> SEQUENCE: 31
cgatcgagct gcatgctaca g 21

<210> SEQ ID NO 32
<211> LENGTH: 21
<212> TYPE: DNA
<213> ORGANISM: Artificial Sequence
<220> FEATURE:
<223> OTHER INFORMATION: example for coding sequence of random peptide

<400> SEQUENCE: 32
gatcgagctg catgctacag c 21

<210> SEQ ID NO 33
<211> LENGTH: 45
<212> TYPE: DNA
<213> ORGANISM: Artificial Sequence
<220> FEATURE:
<223> OTHER INFORMATION: nucleic acid sequence of dominant NP311 epitope

<400> SEQUENCE: 33
gaggggtggc catacatagc ttgtagaaca tcagttgtag ggaga 45

<210> SEQ ID NO 34
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 34

Glu Gly Trp Pro Tyr Ile Ala Cys Arg Thr Ser Val Val Gly Arg
1               5                   10                  15

<210> SEQ ID NO 35
<211> LENGTH: 30

-continued

<212> TYPE: DNA
<213> ORGANISM: Artificial Sequence
<220> FEATURE:
<223> OTHER INFORMATION: nucleic acid sequence of new NP547 epitope

<400> SEQUENCE: 35
gacctgatct tcagaggtcc aaatgtggtg 30

<210> SEQ ID NO 36
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 36

Asp Leu Ile Phe Arg Gly Pro Asn Val Val
1 5 10

<210> SEQ ID NO 37
<211> LENGTH: 14
<212> TYPE: PRT
<213> ORGANISM: Artificial Sequence
<220> FEATURE:
<223> OTHER INFORMATION: random peptide example
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: tyrosine or phenylalanine
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: proline, alanine or serine
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (9)..(9)
<223> OTHER INFORMATION: alanine or proline
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (11)..(11)
<223> OTHER INFORMATION: any amino acid
<220> FEATURE:
<221> NAME/KEY: MISC_FEATURE
<222> LOCATION: (12)..(12)
<223> OTHER INFORMATION: alanine or serine
<220> FEATURE:
<221> NAME/KEY: MISC_FEATURE
<222> LOCATION: (13)..(13)
<223> OTHER INFORMATION: any amino acid

<400> SEQUENCE: 37

-continued

```
Gly Xaa Xaa Xaa Xaa Xaa Xaa Xaa Xaa Xaa Xaa Xaa Xaa Gly
1               5                   10


<210> SEQ ID NO 38
<211> LENGTH: 14
<212> TYPE: PRT
<213> ORGANISM: Artificial Sequence
<220> FEATURE:
<223> OTHER INFORMATION: random peptide

<400> SEQUENCE: 38

Gly Gly Gly Tyr Ser Ala Ser Cys Pro Val Ile Ala Pro Gly
1               5                   10


<210> SEQ ID NO 39
<211> LENGTH: 13
<212> TYPE: PRT
<213> ORGANISM: Artificial Sequence
<220> FEATURE:
<223> OTHER INFORMATION: random peptide

<400> SEQUENCE: 39

Gly Arg Arg Tyr Lys Ala Thr Ala Ser Ile Ala Phe Gly
1               5                   10


<210> SEQ ID NO 40
<211> LENGTH: 14
<212> TYPE: PRT
<213> ORGANISM: Artificial Sequence
<220> FEATURE:
<223> OTHER INFORMATION: random peptide

<400> SEQUENCE: 40

Gly Asn Ile Phe Phe Ile Ser Thr Ala Ser Ile Ala Asn Gly
1               5                   10


<210> SEQ ID NO 41
<211> LENGTH: 14
<212> TYPE: PRT
<213> ORGANISM: Artificial Sequence
<220> FEATURE:
<223> OTHER INFORMATION: random peptide

<400> SEQUENCE: 41

Gly Thr Met Phe Leu Asn Ala Ser Pro Gly Asn Ser Glu Gly
1               5                   10


<210> SEQ ID NO 42
<211> LENGTH: 13
<212> TYPE: PRT
<213> ORGANISM: Artificial Sequence
<220> FEATURE:
<223> OTHER INFORMATION: random peptide

<400> SEQUENCE: 42

Gly Thr Asp Tyr Leu Ser Ala Ala Arg Ser Ser Asp Gly
1               5                   10


<210> SEQ ID NO 43
<211> LENGTH: 14
<212> TYPE: PRT
<213> ORGANISM: Artificial Sequence
<220> FEATURE:
<223> OTHER INFORMATION: random peptide

<400> SEQUENCE: 43
```

-continued

```
Gly Gly Arg Tyr His Arg Pro Leu Pro Cys Ala Ser Pro Gly
1               5                   10


<210> SEQ ID NO 44
<211> LENGTH: 14
<212> TYPE: PRT
<213> ORGANISM: Artificial Sequence
<220> FEATURE:
<223> OTHER INFORMATION: random peptide

<400> SEQUENCE: 44

Gly Arg Gly Tyr Ile Ser Ala Tyr Pro His Phe Ser Ile Gly
1               5                   10


<210> SEQ ID NO 45
<211> LENGTH: 14
<212> TYPE: PRT
<213> ORGANISM: Artificial Sequence
<220> FEATURE:
<223> OTHER INFORMATION: random peptide

<400> SEQUENCE: 45

Gly Gly Ile Phe Asn Arg Ala Leu Pro Ala Pro Ser Lys Gly
1               5                   10
```